(12) United States Patent
Tran

(10) Patent No.: US 11,452,713 B2
(45) Date of Patent: Sep. 27, 2022

(54) CHEMOTHERAPEUTIC METHODS FOR TREATING LOW-PROLIFERATIVE DISSEMINATED TUMOR CELLS

(71) Applicant: University of Florida Research Foundation, Incorporated, Gainesville, FL (US)

(72) Inventor: David Tran, Gainesville, FL (US)

(73) Assignee: University of Florida Research Foundation, Incorporated, Gainesville, FL (US)

(\*) Notice: Subject to any disclaimer, the term of this patent is extended or adjusted under 35 U.S.C. 154(b) by 0 days.

(21) Appl. No.: 16/845,672

(22) Filed: Apr. 10, 2020

(65) Prior Publication Data
US 2020/0237728 A1  Jul. 30, 2020

Related U.S. Application Data

(62) Division of application No. 16/079,649, filed as application No. PCT/US2017/019240 on Feb. 24, 2017, now abandoned.

(60) Provisional application No. 62/301,210, filed on Feb. 29, 2016, provisional application No. 62/429,151, filed on Dec. 2, 2016.

(51) Int. Cl.
| | |
|---|---|
| A61K 39/395 | (2006.01) |
| A61K 31/421 | (2006.01) |
| A61K 45/06 | (2006.01) |
| A61K 47/68 | (2017.01) |
| A61P 35/00 | (2006.01) |
| A61K 31/12 | (2006.01) |
| A61K 39/00 | (2006.01) |
| C07K 16/24 | (2006.01) |

(52) U.S. Cl.
CPC ............ *A61K 31/421* (2013.01); *A61K 31/12* (2013.01); *A61K 39/3955* (2013.01); *A61K 45/06* (2013.01); *A61K 47/6835* (2017.08); *A61K 47/6843* (2017.08); *A61P 35/00* (2018.01); *A61K 47/68* (2017.08); *A61K 2039/505* (2013.01); *A61K 2300/00* (2013.01); *C07K 16/248* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,527,546 A | 6/1996 | Penza et al. | |
| 5,847,103 A | 12/1998 | Fujita | |
| 5,849,283 A | 12/1998 | Ciliberto et al. | |
| 6,300,347 B1 | 10/2001 | Revesz | |
| 6,316,466 B1 | 11/2001 | Goldstein et al. | |
| 6,319,921 B1 | 11/2001 | Cirillo et al. | |
| 6,420,391 B1 | 7/2002 | Konishi et al. | |
| 6,432,962 B2 | 8/2002 | Horneman | |
| 6,498,274 B1 | 12/2002 | Brown et al. | |
| 6,528,315 B2 | 3/2003 | Bureau et al. | |
| 6,555,555 B1 | 4/2003 | Konishi et al. | |
| 6,579,860 B1 | 6/2003 | Koike et al. | |
| 6,579,874 B2 | 6/2003 | Revesz et al. | |
| 6,596,537 B1 | 7/2003 | Kuromaru et al. | |
| 6,608,072 B1 | 8/2003 | Revesz | |
| 6,645,990 B2 | 11/2003 | Askew et al. | |
| 6,664,395 B2 | 12/2003 | Letavic et al. | |
| 6,686,467 B2 | 2/2004 | Brown et al. | |
| 6,696,464 B2 | 2/2004 | McClure et al. | |
| 6,770,643 B2 | 8/2004 | Cox et al. | |
| 6,809,199 B2 | 10/2004 | Doherty et al. | |
| 6,849,639 B2 | 2/2005 | Dominguez et al. | |
| 6,864,255 B2 | 3/2005 | Geuns-Meyer et al. | |
| 6,867,211 B2 | 3/2005 | Striegel et al. | |
| 6,878,714 B2 | 4/2005 | Askew et al. | |
| 6,881,737 B2 | 4/2005 | Buchanan et al. | |
| 6,881,756 B2 | 4/2005 | Gendimenico | |
| 6,891,039 B2 | 4/2005 | Revesz | |
| 6,897,207 B2 | 5/2005 | Cox et al. | |
| 6,919,336 B2 | 7/2005 | Rvesz | |
| 6,921,762 B2 | 7/2005 | Cai et al. | |
| 6,936,632 B2 | 8/2005 | Striegel et al. | |
| 6,939,874 B2 | 9/2005 | Harmange et al. | |
| 6,943,158 B2 | 9/2005 | Chen et al. | |

(Continued)

FOREIGN PATENT DOCUMENTS

| | | |
|---|---|---|
| EP | 1247810 | 10/2002 |
| WO | WO 98/27098 | 6/1998 |

(Continued)

OTHER PUBLICATIONS

June et al., Expert Opin Biol Ther. Oct. 2016;16(10):1303-9. doi: 10.1080/14712598.2016.1217988. Epub Aug. 8, 2016.\*
Lescar, et al. Journal of Biological Chemistry 270.30 (1995): 18067-18076.\*

(Continued)

*Primary Examiner* — Michael Szperka
(74) *Attorney, Agent, or Firm* — Alston & Bird LLP

(57) ABSTRACT

Disclosed herein are chemotherapeutic methods for the treatment of cancer in humans. In at least one specific embodiment, the method can include administering a therapeutic effective amount of one or more p38 inhibitor compound or salt thereof to a human. The method can also include administering a therapeutic effective of one or more IL-6 inhibitor or one or more IL-6 receptor inhibitor or salt thereof to the human. The method can also include administering a therapeutic effective amount of one or more cytotoxic compound or salt thereof to the human.

8 Claims, 19 Drawing Sheets

(56) References Cited

U.S. PATENT DOCUMENTS

| | | |
|---|---|---|
| 6,962,933 B1 | 11/2005 | Ohkawa et al. |
| 6,965,030 B2 | 11/2005 | Goldstein et al. |
| 6,967,210 B2 | 11/2005 | Smith et al. |
| 6,967,254 B2 | 11/2005 | Dominguez et al. |
| 6,995,162 B2 | 2/2006 | Chen et al. |
| 7,005,523 B2 | 2/2006 | Dombroski et al. |
| 7,012,143 B2 | 3/2006 | Dombroski et al. |
| 7,037,923 B2 | 5/2006 | Dombroski et al. |
| 7,056,918 B2 | 6/2006 | Dombroski et al. |
| 7,081,462 B2 | 7/2006 | Goldstein et al. |
| 7,101,868 B2 | 9/2006 | Elbaum et al. |
| 7,101,899 B1 | 9/2006 | Ohkawa et al. |
| 7,102,009 B2 | 9/2006 | Patel et al. |
| 7,105,682 B2 | 9/2006 | Chen et al. |
| 7,115,617 B2 | 10/2006 | Buchanan et al. |
| 7,119,111 B2 | 10/2006 | Huang et al. |
| 7,151,118 B2 | 12/2006 | Angell et al. |
| 7,166,597 B2 | 1/2007 | Alberti et al. |
| 7,166,623 B2 | 1/2007 | Angell et al. |
| 7,179,821 B2 | 2/2007 | Smith et al. |
| 7,183,297 B2 | 2/2007 | Angell et al. |
| 7,189,731 B2 | 3/2007 | Dewdney et al. |
| 7,196,095 B2 | 3/2007 | Biftu et al. |
| 7,196,104 B2 | 3/2007 | Askew, Jr. et al. |
| 7,208,629 B2 | 4/2007 | Angell et al. |
| 7,227,020 B2 | 6/2007 | Cox et al. |
| 7,230,015 B2 | 6/2007 | Smith et al. |
| 7,253,191 B2 | 8/2007 | Laufer et al. |
| 7,259,171 B2 | 8/2007 | Dombroski et al. |
| 7,282,504 B2 | 10/2007 | Armistad et al. |
| 7,285,561 B2 | 10/2007 | Goldstein et al. |
| 7,307,088 B2 | 12/2007 | Huang et al. |
| 7,309,701 B2 | 12/2007 | Holder et al. |
| 7,309,800 B2 | 12/2007 | Angell et al. |
| 7,314,873 B2 | 1/2008 | Doherty et al. |
| 7,320,987 B2 | 1/2008 | Goldstein et al. |
| 7,320,992 B2 | 1/2008 | Tegley et al. |
| 7,321,001 B2 | 1/2008 | Fu et al. |
| 7,348,339 B2 | 3/2008 | Bailey et al. |
| 7,354,944 B2 | 4/2008 | Zeng et al. |
| 7,381,841 B2 | 6/2008 | Kleemann |
| 7,384,963 B2 | 6/2008 | Angell et al. |
| 7,390,820 B2 | 6/2008 | Tegley |
| 7,396,843 B2 | 7/2008 | Angell et al. |
| 7,423,042 B2 | 9/2008 | Boehm et al. |
| 7,432,289 B2 | 10/2008 | Angell et al. |
| 7,439,247 B2 | 10/2008 | Chen et al. |
| 7,452,880 B2 | 11/2008 | Arora et al. |
| 7,462,613 B2 | 12/2008 | Holder et al. |
| 7,470,689 B2 | 12/2008 | Hoelder et al. |
| 7,479,501 B2 | 1/2009 | Collis et al. |
| 7,479,558 B2 | 1/2009 | Callahan et al. |
| 7,504,403 B2 | 3/2009 | Frohn et al. |
| 7,507,734 B2 | 3/2009 | Hoelder et al. |
| 7,507,748 B2 | 3/2009 | Yuan |
| 7,514,564 B2 | 4/2009 | Chen et al. |
| 7,514,566 B2 | 4/2009 | Zeng et al. |
| 7,517,901 B2 | 4/2009 | Gabriel et al. |
| 7,521,563 B2 | 4/2009 | Nakatogawa et al. |
| 7,531,553 B2 | 5/2009 | Di Pietro et al. |
| 7,534,803 B2 | 5/2009 | Smith et al. |
| 7,541,368 B2 | 6/2009 | Borcherding et al. |
| 7,541,383 B2 | 6/2009 | Fu et al. |
| 7,569,571 B2 | 8/2009 | Dong et al. |
| 7,612,094 B2 | 11/2009 | Lee et al. |
| 7,615,562 B2 | 11/2009 | Bollbuck et al. |
| 7,626,030 B2 | 12/2009 | Kim et al. |
| 7,629,363 B2 | 12/2009 | Devadas et al. |
| 7,652,022 B2 | 1/2010 | Floersheimer et al. |
| 7,652,044 B2 | 1/2010 | Dong et al. |
| 7,977,371 B2 | 7/2011 | Kawashima et al. |
| 8,088,817 B2 | 1/2012 | Kawashima et al. |
| 8,614,240 B2 | 12/2013 | Park Choo et al. |
| 8,802,092 B2 | 8/2014 | Nishimoto et al. |
| 9,212,223 B2 | 12/2015 | Smith |
| 9,352,039 B2 * | 5/2016 | Liu .................. A61K 39/3955 |
| 2003/0073706 A1 | 4/2003 | Konishi et al. |
| 2004/0097493 A1 | 5/2004 | Chen et al. |
| 2004/0209903 A1 | 10/2004 | Dewdney et al. |
| 2005/0197352 A1 | 9/2005 | Goldstein et al. |
| 2005/0203091 A1 | 9/2005 | Arora et al. |
| 2006/0084803 A1 | 4/2006 | Chen et al. |
| 2006/0165696 A1 | 7/2006 | Okano et al. |
| 2006/0252784 A1 | 11/2006 | Goldstein et al. |
| 2007/0049633 A1 | 3/2007 | Gabriel et al. |
| 2007/0134242 A1 | 6/2007 | Nishimoto et al. |
| 2007/0167471 A1 | 7/2007 | Dunn et al. |
| 2007/0208065 A1 | 9/2007 | Nakatogawa et al. |
| 2008/0119497 A1 | 5/2008 | Goldstein |
| 2008/0146590 A1 | 6/2008 | Gabriel et al. |
| 2008/0207684 A1 | 8/2008 | Gabriel et al. |
| 2008/0274106 A1 | 11/2008 | Nishimoto et al. |
| 2009/0209577 A1 | 8/2009 | Rucker et al. |
| 2009/0215817 A1 | 8/2009 | Rucker et al. |
| 2009/0239899 A1 | 9/2009 | Mathias et al. |
| 2009/0270350 A1 | 10/2009 | Devadas et al. |
| 2009/0306108 A1 | 12/2009 | Durley |
| 2010/0099675 A1 | 4/2010 | Kawashima et al. |
| 2011/0136794 A1 | 6/2011 | Kawashima et al. |
| 2013/0090480 A1 | 4/2013 | Park Choo et al. |
| 2015/0299710 A1 | 10/2015 | Esashi et al. |

FOREIGN PATENT DOCUMENTS

| | | |
|---|---|---|
| WO | WO 00/07980 | 2/2000 |
| WO | WO 00/07991 | 2/2000 |
| WO | WO 00/10563 | 3/2000 |
| WO | WO 00/12074 | 3/2000 |
| WO | WO 00/17175 | 3/2000 |
| WO | WO 00/17204 | 3/2000 |
| WO | WO 00/18738 | 4/2000 |
| WO | WO 00/20402 | 4/2000 |
| WO | WO 00/25791 | 5/2000 |
| WO | WO 00/31063 | 6/2000 |
| WO | WO 00/31072 | 6/2000 |
| WO | WO 00/39116 | 7/2000 |
| WO | WO 00/40243 | 7/2000 |
| WO | WO 00/41698 | 7/2000 |
| WO | WO 00/55120 | 9/2000 |
| WO | WO 00/55153 | 9/2000 |
| WO | WO 00/56738 | 9/2000 |
| WO | WO 00/59904 | 10/2000 |
| WO | WO 00/63204 | 10/2000 |
| WO | WO 00/64894 | 11/2000 |
| WO | WO 00/71535 | 11/2000 |
| WO | WO 01/10865 | 2/2001 |
| WO | WO 01/21591 | 3/2001 |
| WO | WO 01/30778 | 5/2001 |
| WO | WO 01/34605 | 5/2001 |
| WO | WO 01/37837 | 5/2001 |
| WO | WO 01/38312 | 5/2001 |
| WO | WO 01/38313 | 5/2001 |
| WO | WO 01/38314 | 5/2001 |
| WO | WO 01/47897 | 7/2001 |
| WO | WO 01/57018 | 8/2001 |
| WO | WO 01/64679 | 9/2001 |
| WO | WO 01/70695 | 9/2001 |
| WO | WO 01/74811 | 10/2001 |
| WO | WO 01/90074 | 11/2001 |
| WO | WO 02/16359 | 2/2002 |
| WO | WO 02/32862 | 4/2002 |
| WO | WO 02/40486 | 5/2002 |
| WO | WO 02/42292 | 5/2002 |
| WO | WO 02/46158 | 6/2002 |
| WO | WO 02/058695 | 8/2002 |
| WO | WO 02/059083 | 8/2002 |
| WO | WO 02/060869 | 8/2002 |
| WO | WO 02/072571 | 9/2002 |
| WO | WO 02/072579 | 9/2002 |
| WO | WO 02/076447 | 10/2002 |
| WO | WO 02/083622 | 10/2002 |
| WO | WO 02/085859 | 10/2002 |
| WO | WO 02/092087 | 11/2002 |
| WO | WO 03/002544 | 1/2003 |

(56) References Cited

FOREIGN PATENT DOCUMENTS

| WO | WO 03/008413 | 1/2003 |
| --- | --- | --- |
| WO | WO 03/020715 | 3/2003 |
| WO | WO 03/024971 | 3/2003 |
| WO | WO 03/024973 | 3/2003 |
| WO | WO 03/032970 | 4/2003 |
| WO | WO 03/032971 | 4/2003 |
| WO | WO 03/032972 | 4/2003 |
| WO | WO 03/032980 | 4/2003 |
| WO | WO 03/032986 | 4/2003 |
| WO | WO 03/032987 | 4/2003 |
| WO | WO 03/033457 | 4/2003 |
| WO | WO 03/033482 | 4/2003 |
| WO | WO 03/033483 | 4/2003 |
| WO | WO 03/033502 | 4/2003 |
| WO | WO 03/035638 | 5/2003 |
| WO | WO 03/043988 | 5/2003 |
| WO | WO 03/053967 | 7/2003 |
| WO | WO 03/068747 | 8/2003 |
| WO | WO 03/076405 | 9/2003 |
| WO | WO 03/084539 | 10/2003 |
| WO | WO 03/087087 | 10/2003 |
| WO | WO 03/088972 | 10/2003 |
| WO | WO 03/091229 | 11/2003 |
| WO | WO 03/093248 | 11/2003 |
| WO | WO 03/097062 | 11/2003 |
| WO | WO 03/103950 | 12/2003 |
| WO | WO 2004/010995 | 2/2004 |
| WO | WO 2004/014870 | 2/2004 |
| WO | WO 2004/014900 | 2/2004 |
| WO | WO 2004/014920 | 2/2004 |
| WO | WO 2004/021988 | 3/2004 |
| WO | WO 2004/022712 | 3/2004 |
| WO | WO 2004/024699 | 3/2004 |
| WO | WO 2004/026302 | 4/2004 |
| WO | WO 2004/031188 | 4/2004 |
| WO | WO 2004/032874 | 4/2004 |
| WO | WO 2004/060306 | 7/2004 |
| WO | WO 2004/071440 | 8/2004 |
| WO | WO 2004/073628 | 9/2004 |
| WO | WO 2004/076450 | 9/2004 |
| WO | WO 2006/089798 | 8/2006 |
| WO | WO 2008/023066 | 2/2008 |
| WO | WO 2008/150899 | 12/2008 |
| WO | WO-2013119923 A1 * 8/2013 ......... A61K 39/0011 |
| WO | WO 2017/151409 | 9/2017 |

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Kanyavuz et al., Nat Rev Immunol. Jun. 2019;19(6):355-368. doi: 10.1038/S41577-019-0126-7.*
Mochizuki et al., Oncotarget. Sep. 8, 2015;6(26):22822-35. doi: 10.18632/oncotarget.4477.*
Zhu et al., Tumour Biol. Jan. 2016;37(1):185-97. doi: 10.1007/s13277-015-4450-7. Epub Nov. 24, 2015.*
U.S. Appl. No. 16/079,649, filed Aug. 24, 2018, 2019-0060286, Abandoned.
PCT/US2017/019240, Feb. 24, 2017, WO/2017/151409, Expired.
U.S. Appl. No. 62/429,151, filed Dec. 2, 2016, N/A, Expired.
U.S. Appl. No. 62/301,210, filed Feb. 29, 2016, N/A, Expired.
Adams, J. L. et al., p38 MAP Kinase: Molecular Target for the Inhibition of Pro-inflammatory Cytokines, Elsevier Science, Progress in Medicinal Chemistry, vol. 38 (2001) 1-60.
Adams, J. L. et al., Pyrimidinylimidazole Inhibitors of p38: Cyclic N-1 Imidazole Substituents Enhance p38 Kinase Inhibition and Oral Activity, Bioorangic & Medicinal Chemistry Letters, vol. 11 (2001) 2867-2870.

Aguirre-Ghiso, J. A. et al., Urokinase Receptor and Fibronectin Regulate the ERK$^{MAPK}$ to p38$^{MAPK}$ Activity Ratios That Determine Carcinoma Cell Proliferation or Dormancy In Vivo, Molecular Biology of the Cell, vol. 12 (Apr. 2001) 863-879.
Aguirre-Ghiso, J. A., Models, mechanisms and clinical evidence for cancer dormancy, Nature Publishing Group, vol. 7 (Nov. 2007) 834-846.
Albanyan, E.A. et al., Nonopsonic Binding of Type III Group B Streptococci to Human Neutophils Induces Interleukin-8 Release Mediated by the p38 Mitogen-Activated Protein Kinase Pathway, Infection and Immunity, vol. 68, No. 4 (Apr. 2000) 2053-2060.
Badger, A. M. et al., Disease-Modifying Activity of SB 242235, A Selective Inhibitor of p38 Mitogen-Activated Protein Kinase, in Rat Adjuvant-Induced Arthritis, Artluitis & Rheumatism, American College of Rheumatology, vol. 43, No. 1 (Jan. 2000), 175-183.
Badger, A. M. et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, The Journal of Pharmacology and Experimental Therapeutics, vol. 279, No. 3 (1996) 1453-1461.
Beck, B. et al., Unravelling cancer stem cell potential, Nature Reviews Cancer, vol. 13 (Oct. 2013) 727-738.
Braun, S. et al., A Pooled Analysis of Bone Marrow Micrometastasis in Breast Cancer, The New England Journal of Medicine (2005) 353(8), 793-802.
Duarte, V. M. et al., Curcumin Enhances the Effect of Cisplatin in Suppression of Head and Neck Squamous Cell Carcinoma via Inhibition of IKKβ Protein of the NFκB Pathway, Molecular Cancer Therapeutics, Oct. 2010, vol. 9, 2665-2675.
Eli Lilly and Company "NCT01663857" Nov. 17, 2015, Retrieved from the internet: <URL: https://clinicaltrials.gov/ct2/history/NCT01663857?V_29=View#StudyPageTop>. 14 pages.
Enslen, H. et al., Selective Activation of p38 Mitogen-activated Protein (MAP) Kinase Isoforms by the MAP Kinase Kinases MKK3 and MKK6, The Journal of biological chemistry, vol. 273, No. 3 (1998) 1741-1748.
Guo, Y. et al., Effects of Siltuximab on the IL-6-Induced Signaling Pathway in Ovarian Cancer, Clinical Cancer Research, Aug. 2010, 5759-5769.
International Search Report and Written Opinion for corresponding International Application No. PCT/US2017/019240, dated May 15, 2017, 8 pages.
Kishimoto, T., Interleukin-6: From Basic Science to Medicine—40 Years in Immunology. Annual Review of Immunology (2005) 23, 1-21.
Kruspe, S. et al., Chlorin e6 Conjugated Interleukin-6 Receptor Aptamers Selectively Kill Target Cells Upon Irradiation, Molecular Therapy—Nucleic Acids, Jan. 2014, vol. 3, 1-7.
Liu, S., Breast Cancer Stem Cells Are Regulated by Mesenchymal Stem Cells through Cytokine Networks. Cancer Research 71 (2011) 614-624.
Luzzi, K.J., et al., Multistep Nature of Metastatic Inefficiency: Dormancy of Solitary Cells after Successful Exuavasation and Limited Survival of Early Micrometastases. Am J Pathol, vol. 153, No. 3, 865-873.
Mochizuki, D. et al, Anti-tumor effect of inhibition of IL-6 signaling in mucoepidermoid carcinoma, Oncotarget, Jun. 2015, vol. 6, 22822-22835.
Okuda, Yasuaki, Review of tocilizumab in the treatment of rheumatoid arthritis, Biologies: Targets & Therapy, Mar. 2008, vol. 2, 75-82.
Pereira, L. et al., Inhibition of p38 MAPK sensitizes tumour cells to cisplatin-induced apoptosis mediated by reactive oxygen species and JNK, EMBO Molecular Medicine, Sep. 2013, vol. 5, 1759-1774.
Sosa, M.S. et al., Mechanisms of disseminated cancer cell dormancy: an awakening field, Nat Rev Cancer, vol. 14, (Sep. 2014) 611-622.
Tran, D. D et al., Temporal and Spatial Cooperation of Snaill and Twistl during Epithelial-Mesenchymal Transition Predicts for Human Breast Cancer Recurrence, Molecular Cancer Research, (2011) 9(12) 1644-1657.

(56) References Cited

OTHER PUBLICATIONS

Tran, H.D. et al., Transient SNAIL1 Expression Is Necessary for Metastatic Competence in Breast Cancer, Cancer Research, (2014) 74(21) 6330-6340.

Watson, M.A. et al., Isolation and Molecular Profiling of Bone Marrow Micrometastases Identifies TWIST1 as a Marker of Early Tumor Relapse in Breast Cancer Patients. Clin Cancer Res, (2007) 13(17) 5001-5009.

Dörwald, Florencio Zaragoza. Side Reactions In Organic Synthesis: A Guide To Successful Synthesis Design, Weinheim: WILEY-VCH, Verlag, GmBH & Co., 2005, Preface, (4 pages).

Fujimoto-Ouchi, Kaori et al. Capecitabine Improves Cancer Cachexia And Normalizes IL-6 And PTHrP Levels In Mouse Cancer Cachexia Models, Cancer Chemotherp. Pharmacol, (2007), vol. 59, pp. 807-815. DOI: 10.1007/s00280-006-0338-y.

Bharti, R. et al. Diacerein-Mediated Inhibition Of IL-6/IL-6R Signaling Induces Apoptotic Effects On Breast Cancer. Oncogene, (2016), vol. 35, pp. 3965-3975. Published Online Nov. 30, 2015.

Heo, Tae-Hwe et al. Potential Therapeutic Implications Of IL-6/IL-6R/gp130—Targeting Agents In Breast Cancer, Oncotarget, vol. 7, No. 13, Published Jan. 31, 2016.

\* cited by examiner

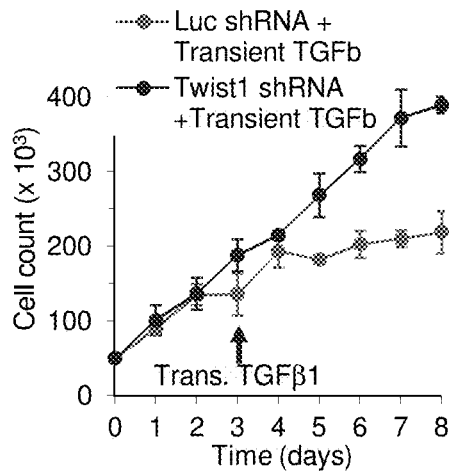
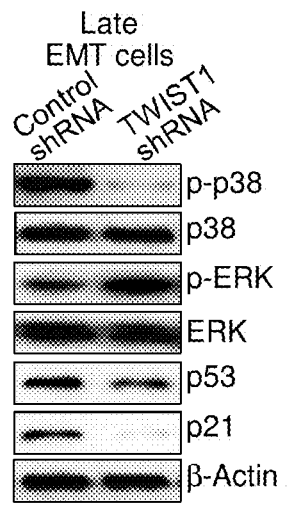
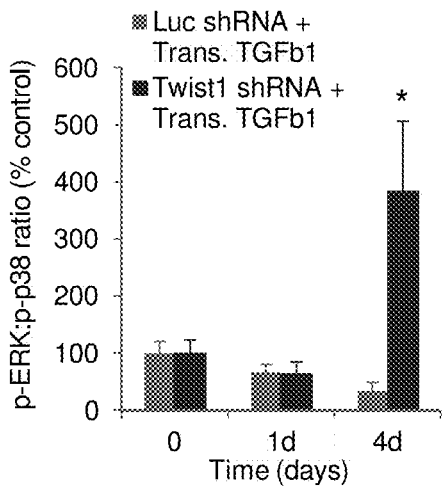
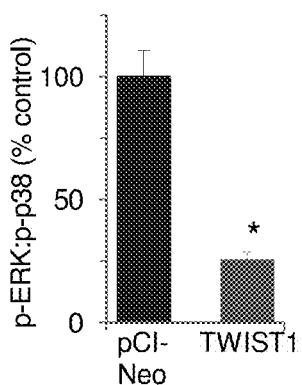
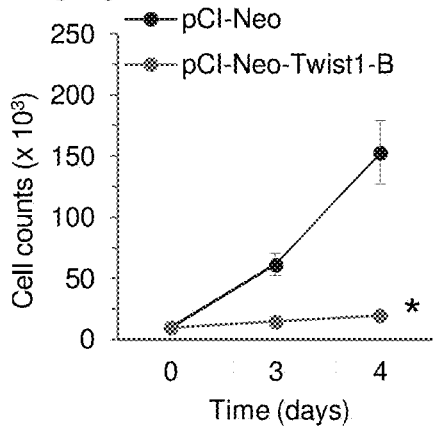
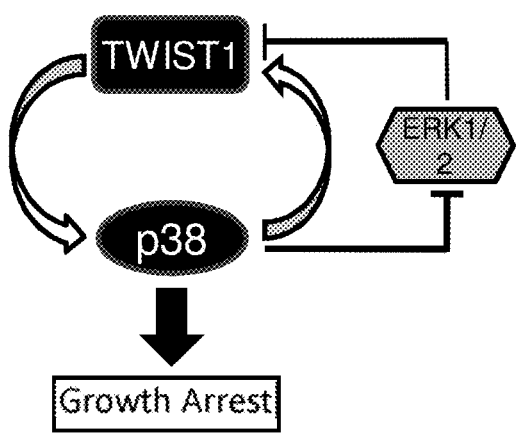

| Paclitaxel (Taxol) IC$_{50}$ (nM) | | |
|---|---|---|
| | Vector | TWIST1 |
| DMSO | 3.3 | >40 |
| SB203580 | 5 | 6.1 |

FIG. 5A
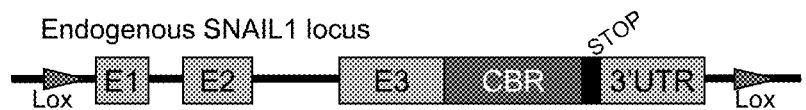
FIG. 5B
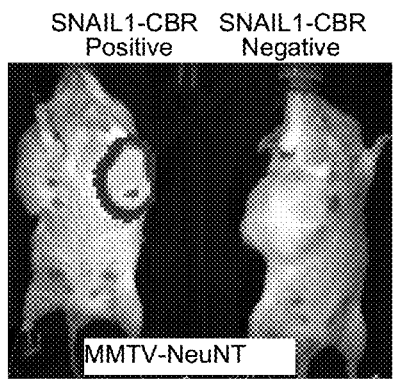
FIG. 5C
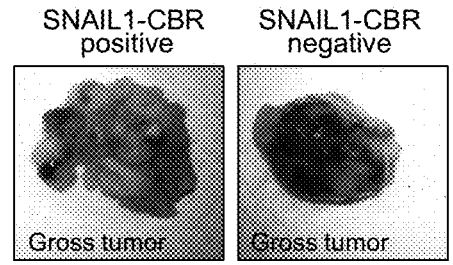
FIG. 5D
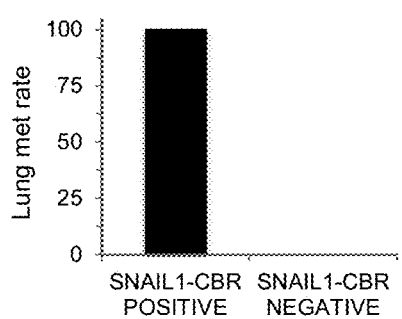
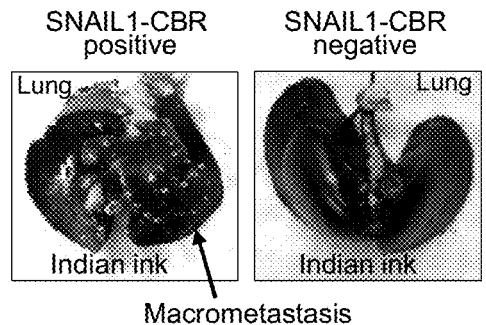
FIG. 5E
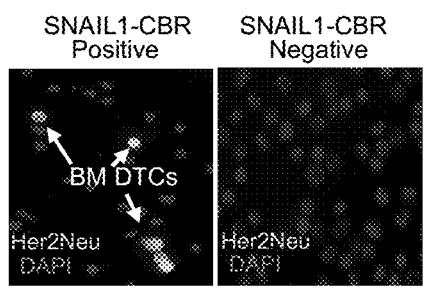
FIG. 5F
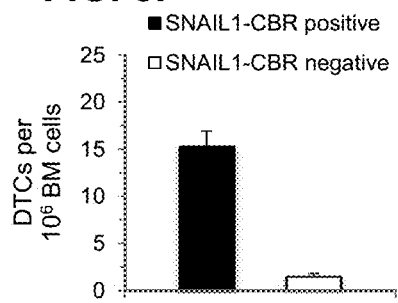

Primary Tumor

FIG. 7A
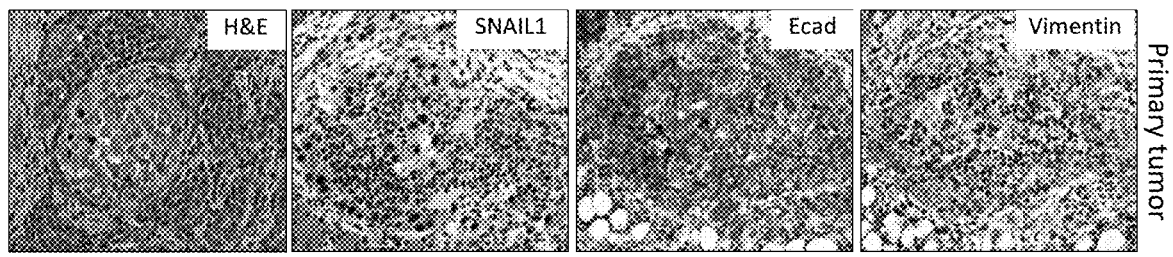
FIG. 7B
FIG. 7C
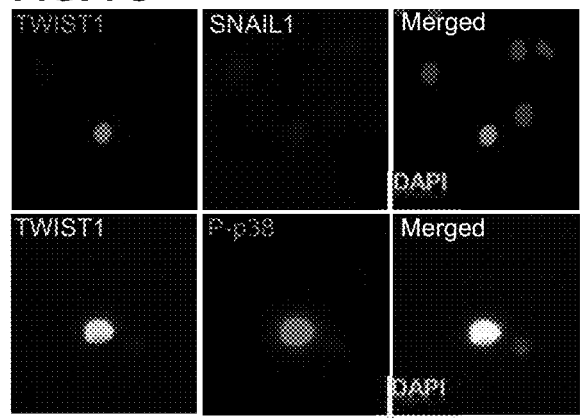
FIG. 7D
| Total ErbB2+ BM DTCs | | | % (Of 100 ErbB2+ BM DTCs) |
|---|---|---|---|
| TWIST1+ | | | 29 |
| | TWIST1+; p-p38+ | | 23 |
| | | BrdU+ | 3 |
| | | BrdU- | 20 |
| | TWIST1+; SNAIL1+ | | 0 |
| TWIST1- | | | 71 |
| | TWIST1-; p-p38- | | 67 |
| | | BrdU+ | 55 |
| | | BrdU- | 12 |
| | TWIST1-; SNAIL1+ | | 2 |

SNAIL1 in primary tumors

SNAIL1 in BM DTCs

TWIST1 in primary tumors

TWIST1 in BM DTCs

TWIST1:SNAIL1 ratio in primary tumors

TWIST1:SNAIL1 ratio in BM DTCs

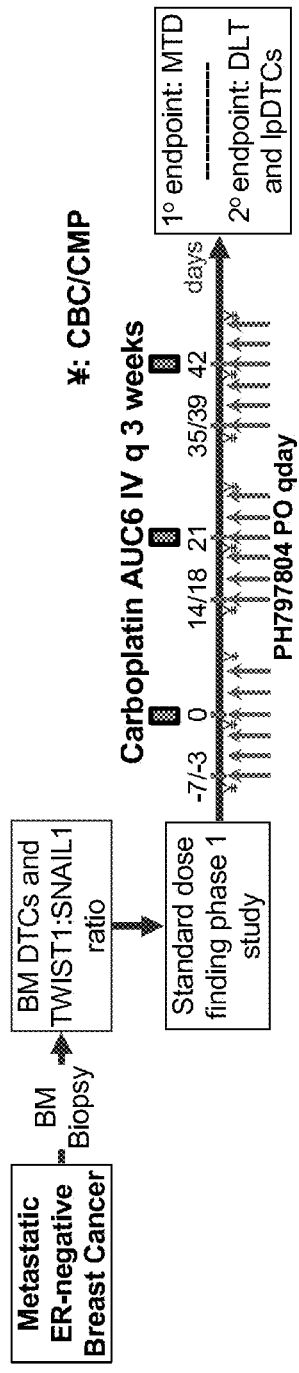

CHEMOTHERAPEUTIC METHODS FOR TREATING LOW-PROLIFERATIVE DISSEMINATED TUMOR CELLS

CROSS-REFERENCE TO A RELATED APPLICATION

This application is a divisional application of U.S. application Ser. No. 16/079,649, filed Aug. 24, 2018, which is the National Stage of International Application No. PCT/US17/19240, filed Feb. 24, 2017, which claims the benefit of U.S. Provisional Application Ser. Nos. 62/301,210, filed Feb. 29, 2016, and 62/429,151, filed Dec. 2, 2016, the disclosures of which are hereby incorporated by reference in their entirety, including all figures, tables and amino acid or nucleic acid sequences.

GOVERNMENT LICENSE RIGHTS

This invention was made with government support under grant number K08 CA160824 and R01 CA238387 awarded by National Institutes of Health and under 6BC04 awarded by the Florida Department of Health. The government has certain rights in the invention.

BACKGROUND

Patients with locally advanced cancer, such as breast, melanoma and kidney cancer, can develop metastatic disease years later, a phenomenon known as tumor dormancy. Tumor dormancy is a poorly understood and significant clinical problem. A major cause of this late metastatic risk is the presence of cancer stem-like cells residing in distant organs after having spread from the primary tumor well before the tumor was treated and surgically removed. These metastatic cells, known as disseminated tumor cells (DTC), are dividing slowly and therefore highly resistant to treatment. These low-proliferative, stem-like DTCs (lpDTCs) can persist in distant organs for an extended period of time before becoming reactivated to form a metastasis. Attempts at eliminating lpDTCs have not been successful due to a poor understanding of their biology and a lack of therapeutic targets. Currently, there is no effective therapy that can eliminate lpDTCs. There is a need, therefore, for new, chemotherapeutic methods that can reactivate lpDTCs and/or cancer stem cells to make them sensitive to chemotherapy.

SUMMARY

Provided are chemotherapeutic methods for the treatment of cancer in humans. In at least one specific embodiment, the method can include administering a therapeutic effective amount of a p38 inhibitor compound or salt thereof to a human, and administering a therapeutic effective of a cytotoxic compound or salt thereof to the human.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIGS. 3A-F show the central role of p38 in EMT maintenance and cellular dormancy. FIG. 3A show late EMT cells are growth arrested, which is dependent on TWIST1. FIGS. 3B and 3C shows TWIST1 depletion in late EMT cells leads to reversal of growth arrest, a high ERK:p38 signaling ratio (i.e. low or inactive p38) and down-regulated of p53 and p21. FIGS. 3D and 3E show the overexpression of TWIST1 leads to a modest reduction ERK:p38 signaling ratio (i.e. activated p38), which in turn results in profound growth arrest ($p<0.05$). FIG. 3F shows a diagram of the TWIST1-p38 signaling axis regulating cellular dormancy.

FIG. 4A shows growth-arrested TWIST1 cells reactivated by p38 inhibition, which renders them more sensitive to the cytotoxic drug, paclitaxel (taxol) (FIG. 4B).

FIGS. 5A-5F show a model of cancer EMT/SNAIL1 reporter (SNAIL1-CBR). FIG. 5A shows the targeting construct. The 3' exon of SNAIL1 is fused in frame with the click beetle red luciferase (CBR), allowing for in vivo detection of SNAIL1. FIGS. 5B-F show the high SNAIL1 expression in primary breast tumors (FIG. 5B) in SNAIL1-CBR/MMTV-NenNT mice correlates with a gross infiltrative phenotype (FIG. 5C), lung metastasis (FIG. 5D) and BM DTCs (FIGS. 5E and 5F).

FIG. 6A show representative images of SNAIL1 IHC of sections of breast tumors isolated from MMTV-PyMT; SNAIL1 KO MMTV-PyMT. Control mice demonstrating efficient SNAIL1 deletion in SNAIL1 KO mice. FIGS. 6B-D show SNAIL1 KO significantly reduced lung metastases (FIGS. 6B and 6C) and BM DTCs (FIG. 6D).

FIGS. 7A-7D show the SNAIL1-TWIST1-p38 axis intact in ErvB2-induced mouse breast cancer model. FIG. 7A shows SNAIL1 is expressed in the primary tumor and associated with EMT changes. FIG. 7B SNAIL1 is rarely detected in BM DTCs, although BM DTCs maintain the EMT phenotype (i.e. low Ecad and high vementin). FIGS. 7C and 7D show TWIST1 expression and p38 activation (p-p38) are high in BM DTCs maintain the EMT phenotype 29/100 (29%) of BM DTCs has high expression of TWIST1. Of these TWIST1+ DTCs, 70%(20/29) has activated p38 and is dormant (BrdU−). In contrast, of TWIST1− BM DTCs, only 17% (12/71) is dormant. These results indicate that the large majority of dormant DTCs has activated p38 and expresses TWIST1.

FIG. 8A shows p38 inhibition (SB203085) increases BM DTC count while Taxol decreases it (*$p<0.05$). FIG. 8B shows that SB203085 decreases the fraction of TWIST1+; p-p38; BrdU− BM DTCs while Taxol enriches it, indicating that TWIST1+; p-p38+, BrdU− DTCs are chemoresistant (*$p<0.05$).

FIGS. 9A and B show the overall survival (A) and total BM DTCs (B) before and after chemo were determined.

FIGS. 10A-10F show the SNAIL1 expression in primary tumors (A), not in DTCs (B), correlates with metastasis. In contrast, TWIST1 expression in DTCs (D), not in primary tumor (C), correlates with metastasis. TWIST1:SNAIL1 ratio in primary tumors does not correlate with distant recurrences (E), but in BM DTCs, the TWIST1:SNAIL1 ratio is high predictive of distant recurrences (p=0.0001) (*p≤0.05).

FIGS. 11A-11C shows Phase 1 dose finding study of PH797804 plus carboplatin in patients with advanced metastatic ER-negative breast cancer who have exhausted all standard treatment. FIGS. 11B and 11C show the dose escalation schedule (B) and timing escalation schedules (C) of PH797804. The starting regimen will be PH797804 3 mg PO day starting 3 days prior to and ending 3 days after carboplatin.

DETAILED DESCRIPTION

Figure 1:
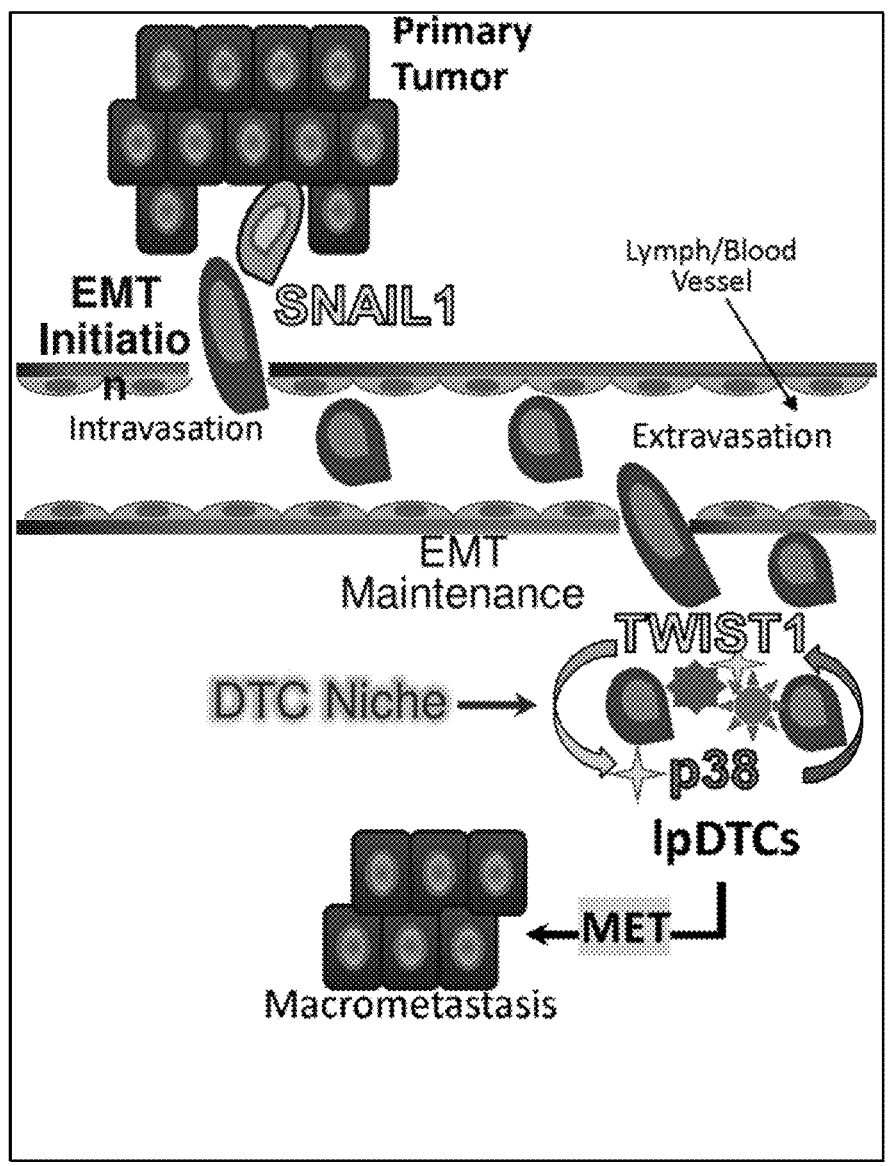
FIG. 1 shows the SNAIL-TWIST1-p38 axis in cancer EMT, low proliferative DTCs, and macrometastasis.

Disclosed herein are chemotherapeutic methods that can include administrating one or more p38 inhibitors and one or more cytotoxic drugs to a human in a particular sequence. The chemotherapeutic method can be used to treat cancers, neoplasms, growths, and/or tumors. Without wanting to be bound by theory, it is believed that this chemotherapeutic method can acutely bring lpDTCs out of quiescence by inhibiting their p38 pathway, which in turn reactivates the lpDTCs' sensitivity to cytotoxic drugs.

The p38 inhibitor and the cytotoxic drug can be administered simultaneously or sequentially. For example, the p38 inhibitor can be administered before and the cytotoxic drug, or, conversely, the cytotoxic drug can be administered before the p38 inhibitor. The chemotherapeutic method can also be used in combination with other therapies. For example, the p38 inhibitor and the cytotoxic drug can be administered before, during, or after surgical procedure and/or radiation therapy. The p38 inhibitor and the cytotoxic drug can also be administered in conjunction with other anticancer agents, non-specific or targeted. The specific amount of the anti-cancer agent will depend on the specific agent used, the type of condition being treated or managed, the severity and stage of the condition, and the amount(s) of compounds and any optional additional active agents concurrently administered to the subject.

p38 (also CSBP or RK) is a serine/threonine mitogen-activated protein kinase (MAPK) that has been shown to regulate pro-inflammatory cytokines. Many forms of p38 MAPK (α, β, γ, δ), each encoded by a separate gene, make up part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNF-α. P38 functions by phosphorylating downstream substrates that include other kinases and transcription factors. Agents that inhibit p38 kinase have been shown to block the production of cytokines including but not limited to TNF-α, IL-6, IL-8 and IL-1β in vitro and in vivo models. See, e.g., Adams, J. L., et al., *Progress in Medicinal Chemistry*, 38: 1-60 (2001).

Any compound useful to inhibit activity of p38 MAPK (i.e., p38 inhibitor) can be used. The p38 inhibitor can include, but is not limited to: PH797804 (3-(4-(2,4-difluorobenzyloxy)-3-bromo-6-methyl-2-oxopyridin-1(2H)-yl)-N,4-dimethylbenzamide); RWJ 67657 (4-[4-(4-Fluorophenyl)-1-(3-phenylpropyl)-5-(4-pyridinyl)-1H-imidazol-2-yl]-3-butyn-1-ol); SCIO 469 (6-Chloro-5-[[(2R,5S)-4-[(4-fluorophenyl)methyl]-2,5-dimethyl-1-piperazinyl]carbonyl]-N,N, 1-trimethyl-α-oxo-1H-Indole-3-acetamide); EO 1428 ((2-Methylphenyl)-[4-[(2-amino-4-bromophenyl)amino]-2-chlorophenyl]methanone); Org 48762-0 ((4,6-Bis(4-fluorophenyl)-2-methyl-5-(4-pyridyl)-2H-pyrazolo[3,4-b]pyridine); SD 169 (5-Carbamoylindole); SB 203580 (4-(4-Fluorophenyl)-2-(4-methylsulfinylphenyl)-5-(4-pyridyl)-1H-imidazole); SB 202190 (4-(4-Fluorophenyl)-2-(4-hydroxyphenyl)-5-(4-pyridyl)-1H-imidazole); SB 239063 (trans-4-[4-(4-Fluorophenyl)-5-(2-methoxy-4-pyrimidinyl)-1H-imidazol-1-yl]cyclohexanol); SB 220025 (4-[5-(4-fluorophenyl)-3-piperidin-4-ylimidazol-4-yl]pyrimidin-2-amine); VX-745 (5-(2,6-Dichlorophenyl)-2-[2,4- difluorophenyl)thio]-6H-pyrimido[1,6-b]pyridazin-6-one); SB 242235 (N-(2,3-Dihydro-7,8-dimethoxyimidazo[1,2-c]quinazolin-5-yl)-3-pyridinecarboxamide); VX-702 (6-[(Aminocarbonyl)(2,6-difluorophenyl)amino]-2-(2,4-difluorophenyl)-3-pyridinecarboxamide); SD-282 (1H-indole-5-carboxamide); PH-797804 (3-[3-bromo-4-[(2,4-difluorophenyl)methoxy]-6-methyl-2-oxopyridin-1-yl]-N,4-dimethylbenzamide); L-167307 (4-[3-(4-fluorophenyl)-5-(4-methylsulfinylphenyl)-1H-pyrrol-2-yl]pyridine); RPR200765A; pamapimod (6-(2,4-difluorophenoxy)-2-(1,5-dihydroxypentan-3-ylamino)-8-methylpyrido[2,3-d]pyrimidin-7-one); BIRB 796; BMS 582949; substituted 2-aza-[4.3.0]-bicyclic heteroaromatic compounds; ARRY-791; SB681323; ISIS101757; SCIO0323; PS540446 (4-[5-(cyclopropylcarbamoyl)-2-methylanilino]-5-methyl-N-propylpyrrolo[2,1-f][1,2,4]triazine-6-carboxamide); SB856553 (6-[5-(cyclopropylcarbamoyl)-3-fluoro-2-methylphenyl]-N-(2,2-dimethylpropyl)pyridine-3-carboxamide); KC706; SB230580; SB281832 (2-[4-(4-fluorophenyl)-5-(2-phenoxypyrimidin-4-yl)imidazol-1-yl]propane-1,3-diol); and Losmapimod (GW856553X) (6-[5-(cyclopropylcarbamoyl)-3-fluoro-2-methylphenyl]-N-(2,2-dimethylpropyl)pyridine-3-carboxamide) or salts thereof.

Any of the above-provided specific p38 inhibiting compounds, as well as further compounds exhibiting p38 inhibiting activity, may be disclosed in additional documents. In particular, any p38 inhibiting compound disclosed in any of the following documents may be used. All of the following documents are incorporated herein by reference in their entirety: Foster M L and Halley F S, Drug News Perspect. (2000) 13:488-497; Newton R and Holden N, Biodrugs (2003) 17: 113-129; Boehm J C and Adams J L, Expert Opin. Ther. Patents (2000) 10: 25-37; Jackson P F and Bullington J L, Curr. Top. Med. Chem. (2002) 2:1011-1020; Adams J L, et al., Bioorg. Med. Chem. Lett. (2001) 11:2867-2870; Revesz L, et al., Bioorg. Med. Chem. Lett. (2004) 14:3595-3599; Revesz L, el al., Bioorg. Med. Chem. Lett. (2000) 10: 1261-1264; Revesz L, et al., Bioorg. Med. Chem. Lett. (2002) 12:2109-2112; Dombroski M A, et al., Bioorg. Med. Chem. Lett. (2004) 14:919-923; McIntyre C J, et al., Bioorg. Med. Chem. Lett. (2002) 12:689-692; Rupert K C, et al., Bioorg. Med. Chem. Lett. (2003) 13:347-350; Ottosen E R, et al., J. Med. Chem. (2003) 46:5651-5662; Revesz L, et al., Bioorg. Med. Chem. Lett. (2004) 14:3601-3605; Liu L, et al., Bioorg. Med. Chem. Lett. (2003) 13:3979-3982; Fitzgerald C E, et al., Nat. Struc. Biol. (2003) 10:764-769; Mavunkel B J, et al., Bioorg. Med. Chem. Lett. (2003) 13:3087-3090; Regan J, et al., J. Med. Chem. (2002) 45:2994-3008; Cumming J C, et al., Bioorg. Med. Chem. Lett. (2004) 14:5389-5394; J. Med. Chem (2002), 45, 4695-4705, Laufer, S. et al., J. Med. Chem, (2003), 46, 3230-3244, Laufer, S. et al., Synthesis, (2007), 253-266, Laufer S. et al., J. Med Chem., (2008), 51, 4122-4149, Laufer S. et al., J. Med. Chem., (2008), 51, 5630-5640, Koch p: et al., Dissertation Claudia Bracht (2010), University of Tuibingen; Aguirre-Ghiso, J. A., Models, Nat Rev Cancer, 2007. 7(11): p. 834-846; Sosa, M. S., P. Bragado, and J. A. Aguirre-Ghiso, Nat Rev Cancer, 2014. 14(9): p. 611-622; Beck, B. and C. Blanpain, Nat Rev Cancer, 2013. 13(10): p. 727-38; Souza, C. M., et al., Pathol Res Pract, 2013. 209(1): p. 24-9; Lu, K., X. Luo, and P. Y. Chen, Int J Biostat, 2008. 4(1): p. Article 9; Wu, J. and X. Xiong, Group Sequential Design for Randomized Phase III Trials under the Weibull Model. J Biopharm Stat, 2014; Kramar, A. and C. Bascoul-Mollevi, Early stopping rules in clinical trials based on sequential monitoring of serious adverse events. Med Decis Making, 2009. 29(3): p. 343-50; Margolin, A. A., et al., ARACNE: an algorithm for the reconstruction of gene regulatory networks in a mammalian cellular context. BMC Bioinformatics, 2006. 7 Suppl 1: p. S7; Rosvall, M. and C. T. Bergstrom, Proc Natl Acad Sci USA, 2008. 105(4): p. 1118-23; Blondel, V., et al., Journal of Statistical Mechanics: Theory and Experiment, 2008. 2008(10): p. P10008; Palla, G., et al., Uncovering the overlapping community structure of complex networks in nature and society. Nature, 2005. 435 (7043): p. 814-8; Tarca, A. L., et al., BMC Bioinformatics, 2012. 13: p. 136; Benjamini, Y., et al., Behav Brain Res, 2001. 125(1-2): p. 279-84; Reiner, A., D. Yekutieli, and Y. Benjamini, Identifying differentially expressed genes using false discovery rate controlling procedures. Bioinformatics, 2003. 19(3): p. 368-75; Lee, J. C., et al., hit. J. Immunopharmacol. 10: 835-843 (1988); Hashimoto, S., et al., J. Pharmacol. Exp. Ther., 293: 370-375 (2001); Beyaert, R., et al., EMBO J., 15: 1914-1923 (1996); E. A., et al., Infect. Immun., 68: 2053-2060 (2000); Caivano, M. and Cohen, P., J. Immunol., 164: 3018-3025 (2000); Maruoka, S., et al., Am. J. Respir. Crit. Care Med., 161: 659-668 (1999); Jackson, J. R., et al., J. Pharmacol. Exp. Ther., 284: 687-692 (1998); Badger, A. M., et al., Arthritis Rheum., 43: 175-183 (2000); Badger, A. M., et al., J. Pharmacol. Exp. Ther., 279: 1453-1461 (1996); and Nishikori, T., et al., Eur. J. Pharm., 451: 327-333 (2002); Salituro, E. G., et al., Current Medicinal Chemistry, 6: 807-823 (1999); Foster, M. L., et al., Drug News Perspect., 13: 488-497 (2000); Boehm, J. D. and Adams, J. L., Exp. Opin. Ther. Patents, 10: 25-37 (2000); Kumar et al., Nature Reviews, 2:717-726 (2003); Brown et al., J. Inflammation 5:22 (2008); Mayer et al., Drug Discovery Today: Therapeutic Strategies 3(1): 49-54 (2006); Regan et al., J. Med. Chem. 2002, 45, 2994-3008.

Additional p38 inhibitors that can be used are discussed and described in U.S. Pat. Nos. 7,101,899, 6,962,933, US2008207684, US2008146590, US2008119497, US2007167471, US2007049633, US2006252784, U.S. Pat. Nos. 7,517,901, 7,285,561, 6,316,466, US2004097493, U.S. Pat. No. 6,943,158, US2004209903, U.S. Pat. No. 7,189,731, US2005203091, U.S. Pat. No. 7,452,880, US2005197352, U.S. Pat. No. 7,081,462, US2006084803, U.S. Pat. Nos. 7,439,247, 6,319,921, 6,867,211, 6,936,632, 7,253,191, WO2008023066, US2009306108, US2009239899, US2009270350, U.S. Pat. No. 7,629,363, US2009215817, US2009209577, U.S. Pat. Nos. 7,037,923, 7,012,143, 7,259,171, 7,005,523, 6,664,395, 6,696,464, 7,056,918, 7,314,873, 7,196,095, 6,809,199, WO03097062, U.S. Pat. Nos. 6,498,274, 6,686,467, 6,881,756, 7,652,044, 7,569,571, 6,579,874, 6,300,347, 7,652,022, 7,615,562, 6,891,039, 6,608,072, 6,919,336, 6,645,990, 7,196,104, 7,504,403, 7,514,566, 6,967,254, 7,321,001, 7,541,383, 7,115,617, 7,354,944, 6,864,255, 6,881,737, 7,390,820, 7,320,992, 6,965,030, 7,320,987, 7,626,030, 6,939,874, 7,307,088, 7,282,504, 7,105,682, 7,101,868, 6,995,162, 7,119,111, 7,507,748, 7,514,564, 7,102,009, 7,531,553, 6,878,714, 6,921,762, 6,849,639, 7,541,368, 7,470,689, 7,309,701, 7,462,613, 7,479,501, 6,770,643, 6,897,207, 7,381,841, 7,227,020, 6,967,210, 6,528,315, 7,179,821, 7,230,015, 7,534,803, 7,309,800, 7,432,289, 7,208,629, 7,166,623, 7,396,843, 7,384,963, 7,183,297, 7,151,118, 7,166,597, 7,423,042, 7,348,339, 7,479,558, 7,612,094, 6,432,962, 7,507,734, WO02/32862; WO02/060869; WO00/10563; WO0/31063; WO00/31072; WO0/39116; WO00/63204; WO01/30778; WO02/072571; WO03/035638; WO00/64894; WO01/10865; WO01/074811; WO02/072579; WO2004/014900; WO2004/026302; WO0/25791; WO00/40243; WO01/34605; WO02/16359; WO01/57018; WO2004/076450; WO003/024973; WO03/024971;

WO01/90074; WO02/083622; WO002/076447; WO02/092087; WO003/008413; WO003/053967; WO03/076405; WO003/091229; WO01/21591; WO03/020715; WO98/27098; WO00/17204; WO00/17175; WO01/70695; WO01/37837; WO01/38312; WO01/38313; WO01/38314; WO01/64679; WO02/058695; WO003/103950; WO2004/024699; WO02/059083; WO003/088972; WO2004/073628; WO003/033502; WO2004/014920; WO2004/031188; WO00/12074; WO00/59904; WO00/71535; WO02/42292; WO02/46158; WO03/043988; WO2004/022712; WO2004/021988; WO2004/032874; WO03/084539; WO00/41698; WO02/085859; WO03/087087; WO2004/060306; WO2004/014870; WO0/20402; WO0/07980; WO00/07991; WO00/18738; WO0/55120; WO0/55153; WO0/56738; WO01/47897; WO02/40486; WO03/002544; WO2004/071440; WO03/032970; WO03/032971; WO03/032972; WO03/032980; WO03/032986; WO03/032987; WO03/033457; WO03/033482; WO2004/010995; WO03/033483; WO03/068747; WO03/093248; WO2006/089798, WO2008/023066, and European Patent No. 01247810, which are incorporated by reference in their entirety.

In one embodiment, the p38 inhibitor is an inhibitor of the IL-6 pathway. An inhibitor of the IL-6 pathway can be, for example, an L-6 inhibitor or an IL-6 receptor (IL-6R) inhibitor. An IL-6 or IL-6R inhibitor can be an inhibitor of activity or expression of IL-6 or IL-6R.

Accordingly, an embodiment of the invention provides a method to treat cancers, neoplasms, growths, and/or tumors by administering an inhibitor of the IL-6 pathway to a subject. Without wanting to be bound by theory, it is believed that this chemotherapeutic method can acutely bring lpDTCs out of quiescence by inhibiting their p38 pathway via inhibition of the IL-6 pathway, which in turn reactivates the lpDTCs' sensitivity to cytotoxic drugs.

Any agent useful to inhibit the activity of IL-6 pathway can be used. An inhibitor of IL-6 pathway inhibitor can include, but is not limited to IL-6 pathway inhibitors discussed and described in United States Patent Application publications 20150299710, 20130090480, 20110136794, 20100099675, 20080274106, 20070208065, 20070134242, 20060165696 and 20030073706 as well as U.S. Pat. Nos. 5,527,546, 5,847,103, 5,849,283, 6,420,391, 6,555,555, 6,579,860, 6,596,537, 7,521,563, 7,977,371, 8,088,817, 8,614,240, 7,977,371, 8,802,092 and 9,212,223. These publications and patents are incorporated herein by reference in their entirety.

In one embodiment, an inhibitor of IL-6 pathway is an aptamer, for example, aptamers discussed and described in U.S. Pat. No. 9,206,429 and Gupta et al. This patent and the publication are incorporated herein by reference in their entirety.

In a further embodiment, the inhibitor of IL-6 pathway is (4S)-3-[(2S,3S)-3-Hydroxy-2-methyl-4-methylene-1-oxononyl]-4-(1-methylethyl)-2-oxazolidinone (LMT-28). In a further embodiment, the inhibitor of IL-6 pathway is curcumin.

In certain embodiments, an inhibitor of the IL-6 pathway is an anti-IL-6 antibody or an IL-6 binding fragment of an anti-IL-6 antibody. The anti-IL-6 antibody can be a polyclonal or a monoclonal antibody. The monoclonal antibody can be a chimeric or humanized antibody. The fragment of an anti-IL6 antibody can be Fab, F(ab')2, Fv or H chain and single chain Fv (scFv) in which Fv or Fv or H chain and L chain are coupled with a suitable linker. Non-limiting examples of anti-IL-6 antibodies or IL-6 binding fragment thereof include Siltuximab, Olokizumab, ALD518 (BMS-945429), C326, Sirukumab, Elsilimomab and Clazakizumab. Additional examples of anti-IL-6 antibodies or IL-6 binding fragments thereof are known to a person of ordinary skill in the art and such embodiments are within the purview of the invention.

In certain embodiments, an inhibitor of the IL-6 pathway is an anti-IL-6R antibody or an IL-6R binding fragment of an anti-IL-6R antibody. The anti-IL-6R antibody can be a polyclonal or a monoclonal antibody. The monoclonal antibody can be a chimeric or humanized antibody. The fragment of an anti-IL-6R antibody can be Fab, F(ab')2, Fv or H chain and single chain Fv (scFv) in which Fv or Fv or H chain and L chain are coupled with a suitable linker. Non-limiting examples of anti-IL-6R antibodies or IL-6R binding fragment thereof include tocilizumab, sarilumab, REGN88 (SAR153191) and ALX-0061. In In one embodiment, the IL-6R inhibitor is a fusion protein of IL-6R with an Fc fragment of IgG. In a further embodiment, the IL-6 pathway inhibitor is soluble gp130-Fc fusion protein.

A therapeutic effective amount of the p38 inhibitor can be from a low of about 5 mg/day, about 10 mg/day, or about 50 mg/day, to a high of about 3,000 mg/day, about 4,000 mg/day, or about 5,000 mg/day. For example, a therapeutic effective amount of the p38 inhibitor can be from about 5 mg/day to about 5,000 mg/day, 5 mg/day to about 2,000 mg/day, about 6 mg/day to about 20 mg/day, about 15 mg/day to about 45 mg/day, about 35 mg/day to about 70 mg/day, about 55 mg/day to about 105 mg/day, about 100 mg/day to about 200 mg/day, about 100 mg/day to about 1,000 mg/day, about 190 mg/day to about 300 mg/day, about 200 mg/day to about 2,500 mg/day about 225 mg/day to about 500 mg/day, about 400 mg/day to about 600 mg/day, about 500 mg/day to about 3,500 mg/day, about 540 mg/day to about 1,000 mg/day, about 750 mg/day to about 2,000 mg/day, about 1,000 mg/day to about 2,000 mg/day, about 1,000 mg/day to about 3,000 mg/day, about 1,500 mg/day to about 4,000 mg/day, about 1,750 mg/day to about 5,000 mg/day, about 3,000 mg/day to about 4,900 mg/day.

The cytotoxic drug can include, but is not limited to: bendamustine, busulfan, carmustine, chlorambucil, cyclophosphamide, dacarbazine, ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed; actinomycin D, dactinomycin, bleomycin, daunorubicin, doxorubicin, doxorubicin (pegylated liposomal), epirubicin, idarubicin, mitomycin, mitoxantrone, etoposide, docetaxel, irinotecan, paclitaxel, topotecan, vinblastine, vincristine, vinorelbine; carboplatin, cisplatin, oxaliplatin, alemtuzamab, bacullus calmette-guerin, bevacizumab, cetuximab, denosumab, erlotinib, gefitinib, imatinib, interferon, ipilimumab, lapatinib, panitumumab, rituximab, sunitinib, sorafenib, temsirolimus, Trastuzumab, clodronate, ibandronic acid, pamidronate, zolendronic acid, anastrozole, abiraterone, amifostine, bexarotene, bicalutamide, buserelin, cyproterone, degarelix, exemestane, flutamide, and folinic acid.

A therapeutic effective amount of the cytotoxic drug can be from a low of about 5 mg/day, about 10 mg/day, or about 50 mg/day, to a high of about 3,000 mg/day, about 4,000 mg/day, or about 5,000 mg/day. For example, a therapeutic effective amount of the cytotoxic drug can be from about 5 mg/day to about 5,000 mg/day, 5 mg/day to about 2,000 mg/day, about 6 mg/day to about 20 mg/day, about 15 mg/day to about 45 mg/day, about 35 mg/day to about 70 mg/day, about 55 mg/day to about 105 mg/day, about 100 mg/day to about 200 mg/day, about 100 mg/day to about 1,000 mg/day, about 190 mg/day to about 300 mg/day, about 200 mg/day to about 2,500 mg/day about 225 mg/day to about 500 mg/day, about 400 mg/day to about 600 mg/day, about 500 mg/day to about 3,500 mg/day, about 540 mg/day to about 1,000 mg/day, about 750 mg/day to about 2,000 mg/day, about 1,000 mg/day to about 2,000 mg/day, about 1,000 mg/day to about 3,000 mg/day, about 1,500 mg/day to about 4,000 mg/day, about 1,750 mg/day to about 5,000 mg/day, about 3,000 mg/day to about 4,900 mg/day.

Suitable biologically active variants comprise one or more analogues or derivatives of the p38 inhibitors and/or the cytotoxic drug. Indeed, a single compound, may give rise to an entire family of analogues or derivatives having similar activity. Accordingly, the analogues and derivatives of such p38 inhibitors and the cytotoxic drugs, can be used.

The p38 inhibitors and the cytotoxic drugs may contain chiral centers, which may be either be the (R) or (S) configuration, or may comprise a mixture thereof. Accordingly, the p38 inhibitors and the cytotoxic drugs also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Some of the compounds described herein can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry: Reactions, Mechanisms and Structure, 4th Ed. (New York: Wiley-Interscience, 1992), which is incorporated herein by reference.

The time between administering the p38 inhibitor and administering the cytotoxic drug can vary widely. The time between administering the p38 inhibitor and administering the cytotoxic drug can be as short as 1 minute, 5 minutes, or 1 hour, to as long as 3 day, 1 week, or 2 weeks. For example, the time between administering the p38 inhibitor and administering the cytotoxic drug can be from about 1 minute to about 30 minutes, about 5 minutes to about 1 hour, 10 minutes to about 3 days, about 1 hour to about 12 hours, about 1 hour to about 1 week, 6 hours to about 1 day, 6 hours to about 2 weeks, 1 day to about 1 week, 12 hours to about 6 days, or about 1 week to about 2 weeks.

The cancer the human is being treated for can include, but is not limited to: breast cancer, such as triple negative breast cancer, pancreas cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, chondrosarcoma, Ewing's sarcoma, malignant fibrous histiocytoma, fibrosarcoma, multiple myeloma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, glioblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, prostate adenocarcinoma, glioblastoma multiforma, leukemias, lymphomas, malignant melanomas, epidermoid carcinomas, and other carcinomas and sarcomas.

EXAMPLES

In order to provide a better understanding of the foregoing discussion, the following non-limiting examples are offered. Although the examples are directed to specific embodiments, they are not to be viewed as limiting the invention in any specific respect.

Example 1—Identification of Signaling Pathway Involved in lpDTCS

A critical signaling pathway was identified in lpDTCs that is responsible for their quiescence and treatment resistance. This pathway consists of a circular signaling loop involving the p38 MAPK and TWIST1 proteins, both of which have been found to regulate breast cancer metastasis. It was demonstrated that the TWIST1-p38MAPK axis was required for growth arrest in lpDTCs, and that inhibiting this axis was sufficient to reactivate lpDTCs and resensitize them to cytotoxic chemotherapy.

Evidence for lpDTCs in the bone marrow (BM) has been found in metastasis-free patients at diagnosis. A recent meta-analysis found that >30% of localized breast cancer patients (and higher with more aggressive subtypes) had BM lpDTCs at diagnosis and that this predicted for reduced overall survival. Braun, S., et al., *A pooled analysis of bone marrow micrometastasis in breast cancer* N Engl J Med, 2005 353(8): p. 793-802. Experimental work has suggested that rate-limiting steps in metastasis are the ability of lpDTCs to remain viable in foreign tissues and reactivation of their proliferation. See, e.g., Luzzi, K. J., et al., *Multistep nature of metastatic inefficiency: dormancy of solitary cells after successful extravasation and limited survival of early micrometastases*. Am J Pathol, 1998 153(3):p. 865-73.

Figure 2A:
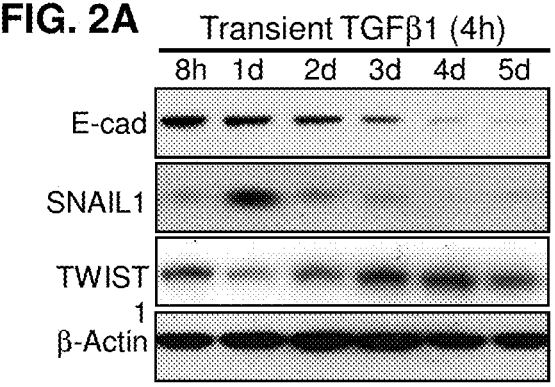
FIGS. 2A-2D show transient TGFbeta induced EMT in epithelial cells. SNAIL1 is only transiently expressed during initiation, suggesting that some other factor maintains EMT (A and B, and depicted in C). TWIST1 level rises in late EMT (A), suggesting it as a likely candidate for maintaining EMT. (D) TWIST1 is required to maintain EMT in MCF10A cells (Ecad repression) in response to transient TGFβ (4 h).
Figure 2B:
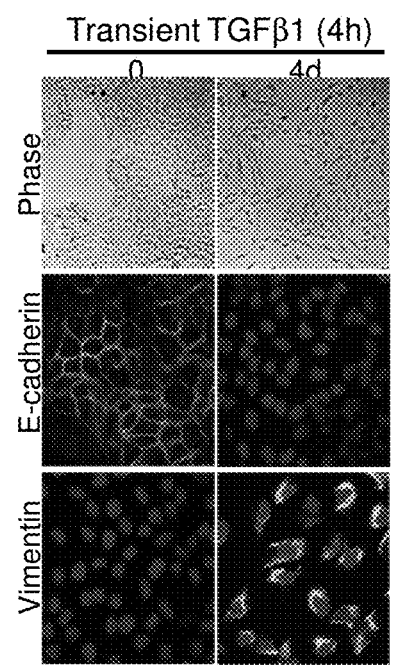
Figure 2C:
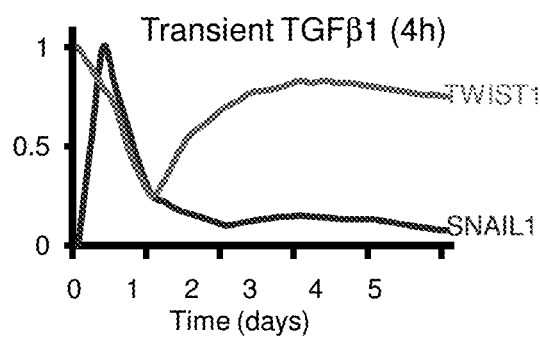
Figure 2D:
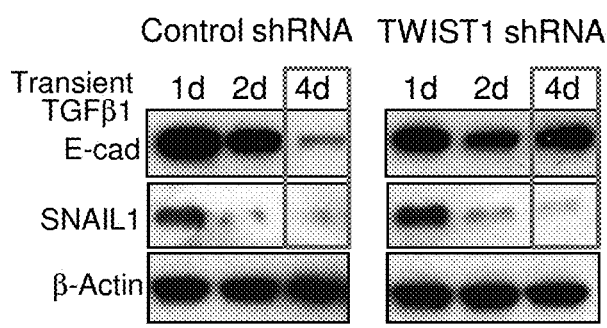

To determine how the presence of multiple EMT-inducing factors regulates cancer EMT, while avoiding potential overexpression, a relevant cell system that would undergo EMT following transient treatment with EMT-inducing cytokines was searched. It was found that many human mammary epithelial cell lines, both normal and transformed, undergo EMT when exposed to physiologic, transient TGFβ1 treatment (4 h) (by morphology, repression of epithelial E-cadherin and induction of mesenchymal Vimentin) (FIG. 2). SNAIL1 was uniquely required for EMT initiation although it was only transiently expressed (FIG. 2A-B and not shown). This suggested that SNAIL1 initiated EMT but some other factor was required to maintain it. The most likely candidate was TWIST1, as its level was inversely correlated with SNAIL1 during EMT (FIG. 2C). Mechanistically, it was shown earlier that SNAIL1 transcriptionally repressed TWSIT1 expression during EMT initiation; however TWIST1 became upregulated in late EMT as SNAIL1 level diminished (FIG. 2). To test whether TWIST1 is required to maintain EMT, several EMT factors were selectively RNAi-depleted in several normal and cancer epithelial cells, followed by treatment with physiologic transient TGFβ1. It was found that TWIST1 was uniquely required to maintain E-cadherin downregulation in late EMT (FIG. 2D).

Since the ERK:p38 signaling ratio has been implicated in regulating DTCs' survival, it was asked whether one of the functions for TWIST1 in maintaining EMT could be through regulation of p38 and ERK activity. During transient TGFβ1-induced EMT, phospho-p38 levels increased while phospho-ERK levels decreased (low ERK:p38 ratio), a scenario favoring prolonged growth arrest. Indeed p53 was increased, p21 induced and cells growth arrested (FIG. 3A-B, quantified in 3C, control Luc shRNA). RNAi-depletion of TWIST1 resulted in low phospho-p38, high phospho-ERK, low p53 and p21 suggesting that growth arrest did not ensue (FIG. 3A-B, quantified in 3C, TWIST1 shRNA). It was hypothesize that TWIST1 may, in some manner, induce a positive feed-forward loop that enhances p38 activity while weakening ERK1/2 signaling. This circular signal feedback could then amplify and propagate the resultant growth arrest critical for EMT maintenance (FIG. 3F). If so, then small changes in either TWIST1 or p38 activity should have a profound impact on the severity of growth arrest.

TWIST1 was overexpressed so as to achieve maximal TWIST1 effect, thereby avoiding the confounding problem of added TGFβ1. TWIST1 overexpression alone generated vigorous TGFβ1-independent EMT and led to 2-3 fold lower ERK:p38 signaling ratio (i.e. high p38 activity) compared to the empty vector (FIG. 3D). This modest increase in p38 activity resulted in greatly enhanced signal output as evidenced by markedly higher rate of growth arrest in TWIST1-overexpressing cells (FIG. 3E).

Figure 4A:
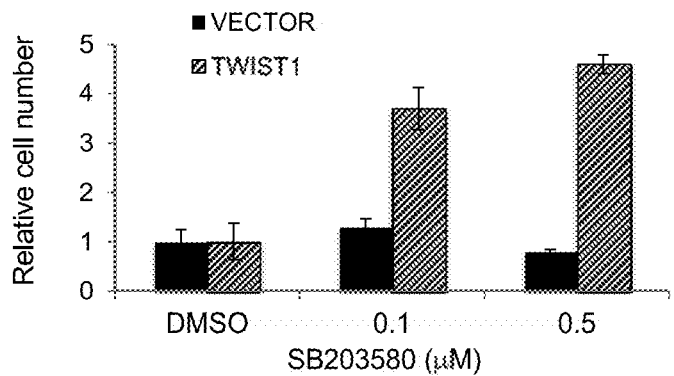
FIGS. 4A-4B.
Figure 4B:
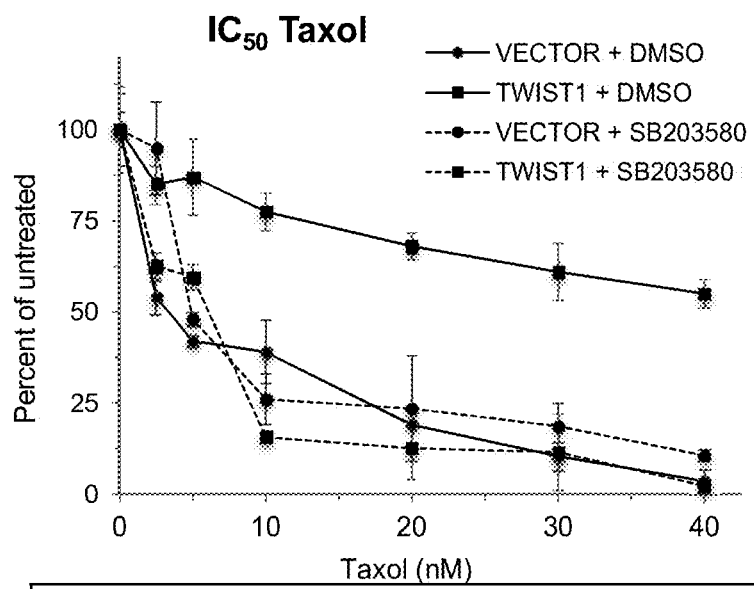

Effective inhibition of p38 activity alone using the specific and potent p38 inhibitor SB203580, an imidazole derivative, reversed TWIST1-dependent growth arrest in a dose dependent manner (FIG. 4A). Furthermore, pretreatment with SB203580 rendered TWIST1-positive cells exquisitely sensitive to Taxol as compared to the non-pretreated (IC50=6.1 nM vs. >40 nM, respectively) (FIG. 4B). Overall, these results suggest the following model: SNAIL1 is required to initiate EMT while TWIST1, dispensable for initiation, is required to maintain it. SNAIL1 represses TWIST1 during EMT initiation. TWIST1 maintains EMT by creating a low ERK:p38 signaling ratio (high p38 activity). Thus high SNAIL1 levels in primary tumors would induce EMT while high TWIST1 levels would maintain EMT in metastatic cells and possibly contribute to lpDTCs in metastatic sites (FIG. 1).

To visualize EMT initiation in vivo in real time and to establish a model which can reliably identify tumors with high propensity to metastasize and give rise to BM lpDTCs, there was generated a SNAIL1 reporter mouse by fusing the SNAIL1 locus in frame with click beetle red luciferase (SNAIL1-CBR) (FIG. 5A). SNAIL1-CBR is properly regulated in both normal (i.e. gastrulation) and pathologic (i.e. liver fibrosis) EMT. See id. After introducing this allele into both ErbB2 and PyMT-induced breast cancer models (MMTV-neuNT and MMTV-PyMT), which produce ER/PR-negative/Her2neu-positive and triple negative breast tumors, respectively, we followed SNAIL-CBR expression during breast tumor progression in the double-transgenic mice by repeated bioluminescence imaging. SNAIL1-CBR positive tumors had irregular shapes and were infiltrative both grossly and microscopically, whereas SNAIL1-CBR negative tumors were round and well encapsulated (FIG. 5B-C and [7]). See id. Mice with SNAIL1-CBR+ breast tumors developed BM DTCs and lung metastasis at a much higher rate compared to those having only SNAIL1-CBR negative tumors (FIG. 5D-F). See id.

Figure 6A:
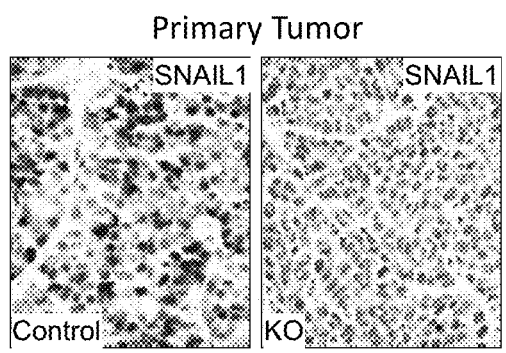
FIGS. 6A-6D show the SNAIL1 requirement for breast tumor metastasis in MMTV-PyMT mice.
Figure 6B:
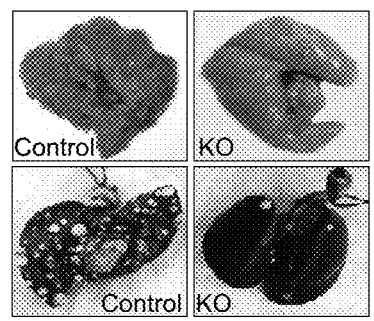
Figure 6C:
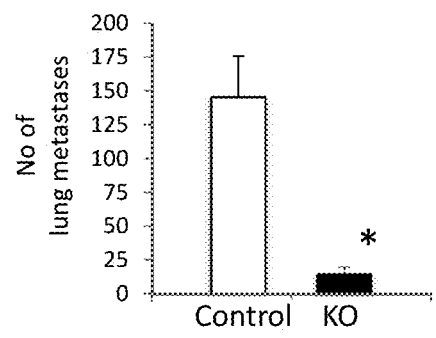
Figure 6D:
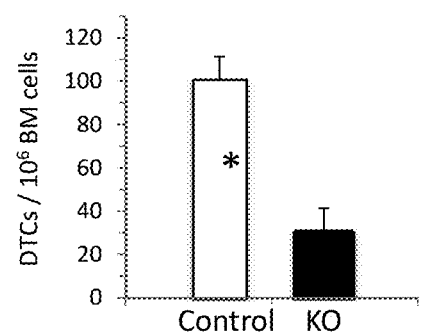

To determine whether SNAIL1 was necessary for breast cancer metastasis, a previously characterized floxed SNAIL1 mouse in the MMTV-PyMT model was made. Deletion of SNAIL1 in primary tumors using the MMTV-cre allele and the resultant reversal of EMT-related molecular changes were verified by IHC for SNAIL1, E-cadherin and Vimentin (FIG. 6A). See, e.g., Rowe, R. G., et al., *Mesenchymal cells reactivate Snail1 expression to drive three-dimensional invasion programs*. The Journal of Cell Biology, 2009. 184(3): p. 399-408. Loss of SNAIL1 resulted in a profound reduction in numbers of lung macrometastases (FIG. 6B-C) and BM DTCs (FIG. 6D), compared to control mice. In addition, most of the few lung macrometastases present in SNAIL1 KO mice were found to arise from SNAIL1-positive cells that escaped CRE-mediated SNAIL1 deletion due to tissue mosaicism of the MMTV promoter. See, e.g., Tran, H. D., et al., *Transient SNAIL1 Expression Is Necessary for Metastatic Competence in Breast Cancer*, Cancer Research, 2014. 74(21): p. 6330-6340.

In summary, SNAIL1 is required for cancer EMT initiation in primary tumors and breast cancer metastasis. Importantly, SNAIL expression and EMT-associated molecular changes were readily detectable in multiple invasive projections in SNAIL1-CBR positive tumors, as compared to SNAIL1-CBR negative tumors. In contrast, SNAIL1 expression was rarely found in BM DTCs, which retained mesenchymal traits (i.e. loss of Ecad and gain of Vimentin) (FIG. 7A-B), indicating that SNAIL1 expression was restricted to the invasive front of primary tumors because of its main role as an EMT initiator, and that some other EMT factor(s) must have supplanted SNAIL1 in secondary organs. See, e.g., Tran, H. D., et al., *Transient SNAIL1 Expression Is Necessary for Metastatic Competence in Breast Cancer*. Cancer research, 2014. 74(21): p. 6330-6340. In fact, similar to our earlier findings in cell lines, while SNAIL1 was undetectable in the vast majority of BM DTCs (~2%) in these models, high TWIST1 expression was found in 29% (29/100) of BM DTCs (FIG. 7C-D).

Figure 8A:
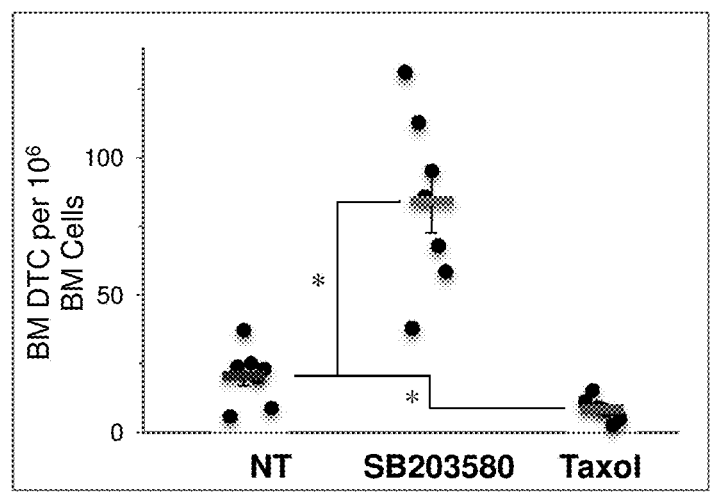
FIGS. 8A-8B show the dormant TWIST1+; p-p38; BrdU- DTCs resistance to cytotoxic drugs in ErbB2-induced mouse breast cancer model.
Figure 8B:
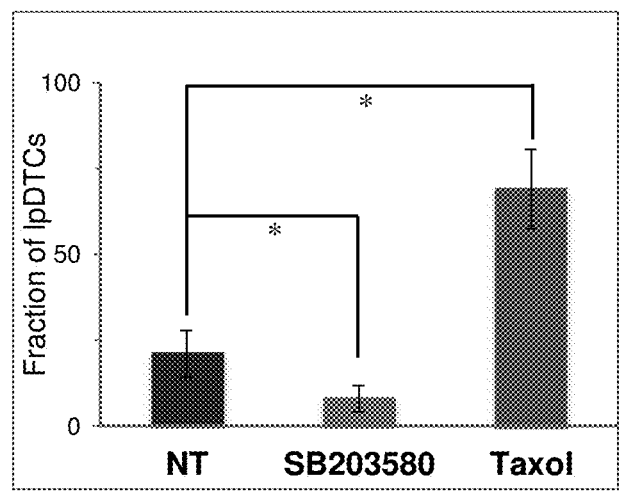

Of these TWIST1-positive BM DTCs, nearly 80% (23/29) expressed activated p38 (p-p38) and 70% (20/29) were also growth arrested as measured by a lack of BrdU incorporation (FIG. 7C-D). In contrast, of the TWIST1-negative DTCs, 94% (67/71) lacked activated p38 and 77% (55/71) were also actively proliferating. Therefore TWIST1-positive; p-p38-positive; BrDU-negative cells represent the fraction of true lpDTCs in these models. To confirm that these BM lpDTCs were resistant to cytotoxic agents and that p38 plays a critical role in their growth arrest, these mice were treated with either SB203085 (10 μmol/kg IP BID×7 days) or the cytotoxic drug paclitaxel (Taxol, 10 mg/kg IP once) and measured the number of all BM DTCs and the fraction of lpDTCs (ratio of TWIST1+; p-p38+; BrdU-DTCs over total BM DTCs). Inhibition of p3 alone was sufficient to increase the number of total BM DTCs>4 fold compared to non-treated animals, whereas treatment with Taxol decreased total DTC number by nearly 2.5 fold, but not to zero, indicating that the remaining BM DTCs remaining after Taxol treatment were likely resistant lpDTCs. In fact, the fraction of BM lpDTCs decreased with SB203085 treatment but significantly increased with Taxol treatment (FIG. 8), suggesting that p38 was important in maintaining chemoresistant lpDTCs and that p38 inhibition forced lpDTCs to downregulate TWIST1 and exit growth arrest. To definitively prove that reawakened lpDTCs through p38 inhibition rendered them sensitive to cytotoxic chemotherapy again, breast cancer mice were treated with either Taxol alone or a combination SB203085 and Taxol and measured both the number of BM DTCs and overall survival. ErbB2- or PyMT-induced breast tumor mice were untreated or treated with either Taxol alone or a combination of SB203085 plus Taxol with SB203085 starting 72 hrs prior to and ending 72 hrs after each dose of Taxol (FIG. 9). Three 21-day cycles of chemotherapy were given. Total BM DTCs were determined prior to and 1 week after treatment ended.

Figure 9A:
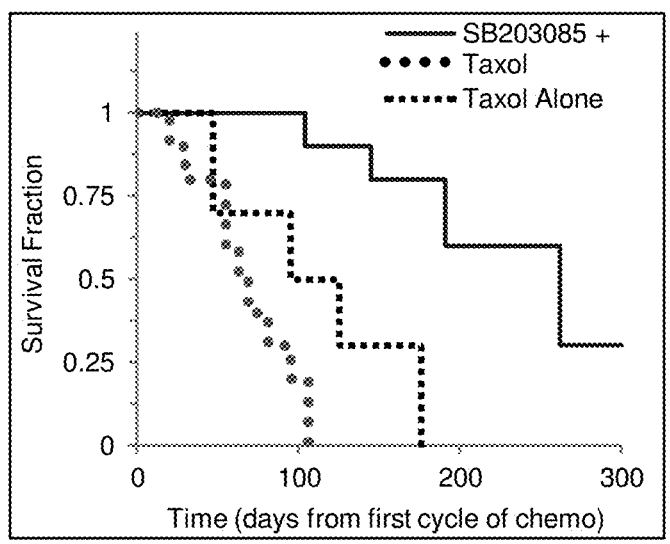
FIGS. 9A-9B show the p38 inhibition increase the DTCs' sensitivity to cytotoxic chemotherapy. DTCs-bearing PyMT-induced breast tumor mice were either untreated or treated with Taxol alone (10 mg/kg) or with SB203085 (10 µg/kg) followed by Taxol. Taxol was given IP every 3 weeks for 3 cycles. SB203085 was given IP BID starting 72 hours prior to Taxol and continuing until 72 hours after Taxol infusion. Ten mice were included in each reference group.
Figure 9B:
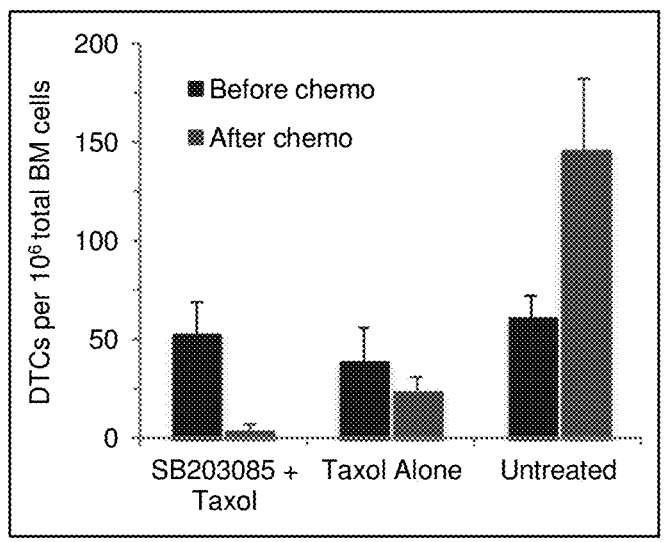

Both MMTV-ErbB2 and MMTV-PyMT mice were used and similar results were obtained for both mouse strains. Results from MMTV-PyMT mice, which produce TNBC, were shown in FIG. 9. Pretreatment with SB203085 significantly reduced total BM DTCs and increased overall survival, compared to Taxol alone and untreated controls (FIG. 9A-B).

Taken together, these results paint a coherent picture tying p38 activity to the TWIST1-dependent EMT maintenance of lpDTCs that eventually leads to early relapses in ER/PR-negative breast cancer. Pharmacologic inhibition of p38 profoundly reversed growth arrest phenotype of lpDTCs, effectively resensitizing them to killing by cytotoxic drugs, and making it possible to eliminate these stem-like lpDTCs—the main source of early relapses in high-risk breast cancer. These results also support the hypothesis that cytotoxic chemotherapy is more effective with minimal residual disease that is acutely forced to proliferate as in reactivated lpDTCs and thus favor the reactivation strategy. To test the clinical merits of the spatiotemporal SNAIL1-TWIST1 cooperation model, EMT factors' transcript levels in primary human breast tumors were determined and matched to BM DTCs of the same pretreated, locally invasive breast cancer patients. See, e.g., Watson, M. A., et al., *Isolation and molecular profiling of bone marrow micrometastases identifies TWIST1 as a marker of early tumor relapse in breast cancer patients.* Clin Cancer Res, 2007 13(17): p. 5001-9.

Figure 10A:
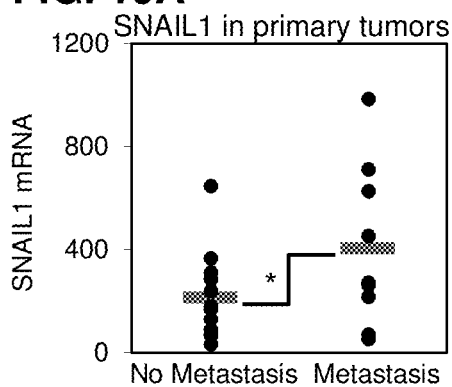
FIGS. 10A-10F show the TWIST1:SNAIL1 ratio in bone marrow DTCs of human patients with clinically localized breast cancer.
Figure 10B:
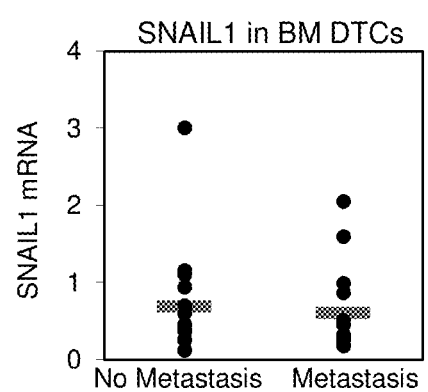
Figure 10C:
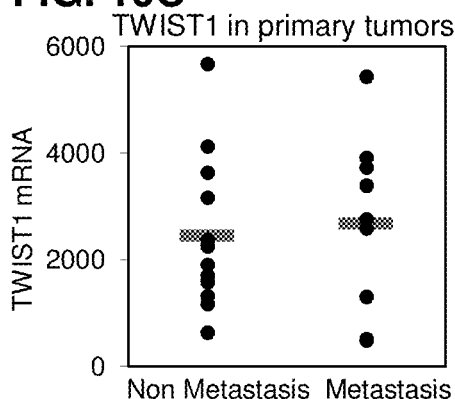
Figure 10D:
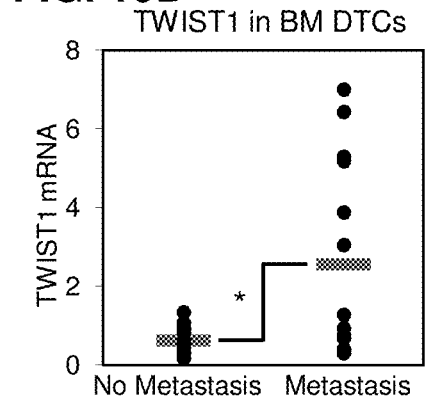
Figure 10E:
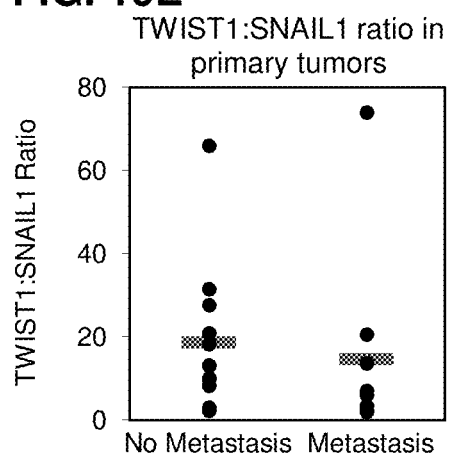
Figure 10F:
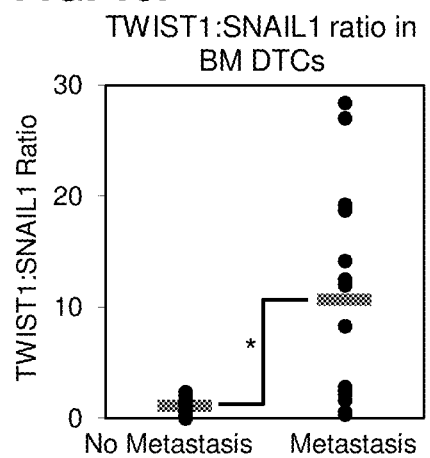
Figure 12:
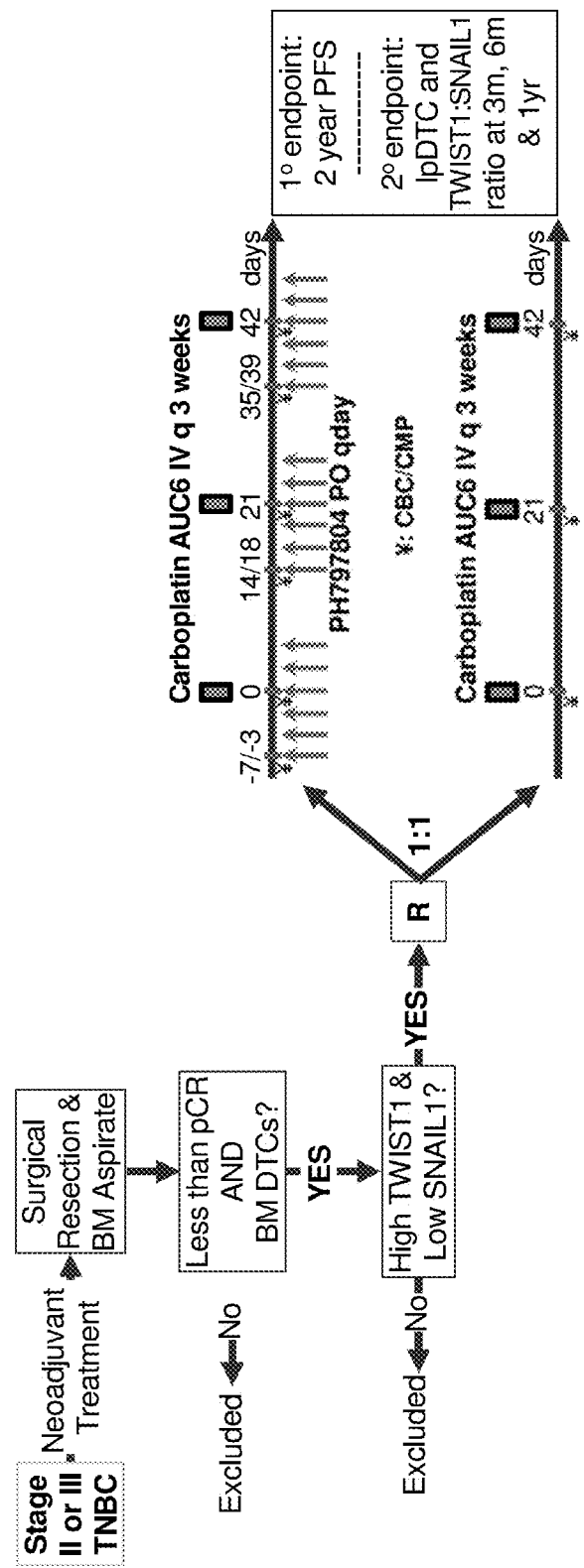
FIG. 12 shows Phase 2, randomized, controlled, open-labeled study of adjuvant PH797804 plus carboplatin versus carboplatin alone in stage II or III TNBC with less than a pathologic complete response (pCR) and with TWIST1-positivelpDTCs. Dose and timing of PH797804 in combination with carboplatin will be per the phase 1 results. pCR=pathologic complete response; BM DTC=bone marrow disseminated tumor cell; lpDTC=low-proliferative disseminated tumor cell; R=randomization; PFS=progression/recurrence-free survival.

In agreement with published data, high SNAIL1 level in primary tumors predicted for distant relapses (FIGS. 10A and 10C and not shown), whereas the level of TWIST1, and other EMT factors, in primary tumors did not (FIG. 10B). See, e.g., Tran, D. T. C., C. A. S.; Biswas, H; Aft, R. L.; Longmore, G. D., *Temporal and Spatial cooperation of Snail1 and Twist1 during Epithelial-Mesenchymal Transition predicts for human breast cancer recurrence.* Molecular Cancer Research, 2011 9(12):p. 1644-57. However, in 30 matched paired primary tumors and BM DTCs, elevated TWIST1 level in BM DTCs was strongly predictive for recurrences within 2 years of initial diagnosis (FIG. 10D), whereas the level of SNAIL1 (low), or other EMT inducers, did not (FIG. 10B and not shown). Approximately 70% of the patient cohort had ER-negative tumors. In summary, the TWIST1:SNAIL1 ratio specifically in BM DTCs strongly predicted for 2 year relapses (FIG. 10E-F).

p38MAPK has been demonstrated to regulate the expression of various inflammatory mediators and, as a result, several p38 inhibitors have been developed to treat inflammatory diseases such as autoimmunity and emphysema and currently are undergoing human phase I and II clinical trials. See, e.g., MacNee, W., et al., *Efficacy and safety of the oral p38 inhibitor PH-797804 in chronic obstructive pulmonary disease: a randomised clinical trial.* Thorax, 2013. 68(8): p. 738-745; Cohen, S. and R. Fleischmann, *Kinase inhibitors: a new approach to rheumatoid arthritis treatment.* Current Opinion in Rheumatology, 2010. 22(3): p. 330-335. There are four p38 isoforms. The alpha isoform and to a minor extent, the beta isoform, which are widely expressed and the primary targets of SB203580, are thought to be the main isoforms that regulate inflammatory mediators and EMT-induced growth arrest. See, e.g., Aguirre-Ghiso, J. A., et al., *Urokinase receptor and fibronectin regulate the ERK (MAPK) to p38(MAPK) activity ratios that determine carcinoma cell proliferation or dormancy in vivo.* Mol Biol Cell, 2001 12(4): p. 863-79; Enslen, H., J. Raingeaud, and R. J. Davis, Selective activation of p38 mitogen-activated protein (MAP) kinase isoforms by the MAP kinase kinases MKK3 and MKK6. The Journal of biological chemistry, 1998. 273(3): p. 1741-8; Eyers, P. A., et al., Conversion of SB 203580-insensitive MAP kinase family members to drug-sensitive forms by a single amino-acid substitution. Chemistry & biology, 1998. 5(6): p. 321-8.

The gamma and delta isoforms have more restricted expression and are less well understood. Most human ready p38 inhibitors currently in clinical studies selectively target alpha with minimal to negligible effect on beta. However, since the beta isoform cannot be ruled out by our preliminary data as playing a role in lpDTCs, especially whether there is a compensatory upregulation of beta once alpha is inhibited, it is essential to select a human ready p38 inhibitor that can inhibit both alpha and beta. PH797804, a novel pyridinone inhibitor of p38, is one of the most advanced p38 inhibitors in human clinical trials. Unlike other p38alpha inhibitors with >20 fold less selectivity for beta, PH797804 is a potent and highly selective inhibitor of alpha with IC50 of 26 nM yet retains reasonable inhibitory effect on beta (IC50 of 102 nM). In a phase 2 clinical trial of PH797804 in emphysema, PH797804 was well tolerated across all 4 dose levels (0.5, 3, 6, and 10 mg PO qday). No significant severe adverse events were reported. The most common side effect was skin rash (~1%). It is commercially available and clinical grade PH797804 is manufactured by Pfizer.

The preclinical data strongly support that treatment-resistant lpDTCs can be reactivated by inhibiting the TWIST1-p38 axis and that, as they are reentering the cell cycle, reactivated lpDTCs become exquisitely susceptible to killing by cytotoxic chemotherapy. It was demonstrated that when mice with detectable lpDTCs were pre-treated with a potent inhibitor of p38 followed by treatment with a cytotoxic drug, the number of BM DTCs and the rate of macrometastases were significantly reduced and overall survival greatly increased when compared to mice treated with the cytotoxic drug alone.

Example 2—IL-6 in Twist1-P38 Axis in Low Proliferative DTCS

Figure 13:
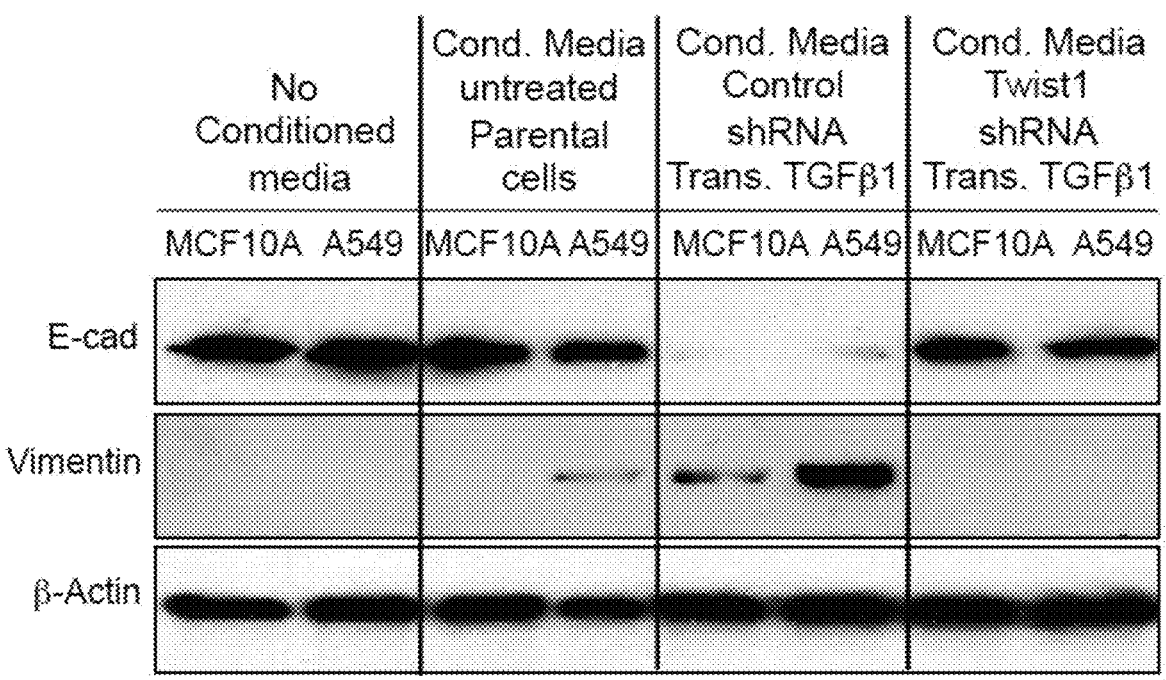
FIG. 13. Secreted cytokines that maintain EMT require Twist1. MCF10A and A549 cells were transduced with a lentivirus expressing control or Twist1 shRNA, then treated with transient TGFβ1. Conditioned media were obtained from d4 cultures and used to treat parental cells, and EMT status determined. Conditioned media from parental cells served as negative control.
Figure 14A:
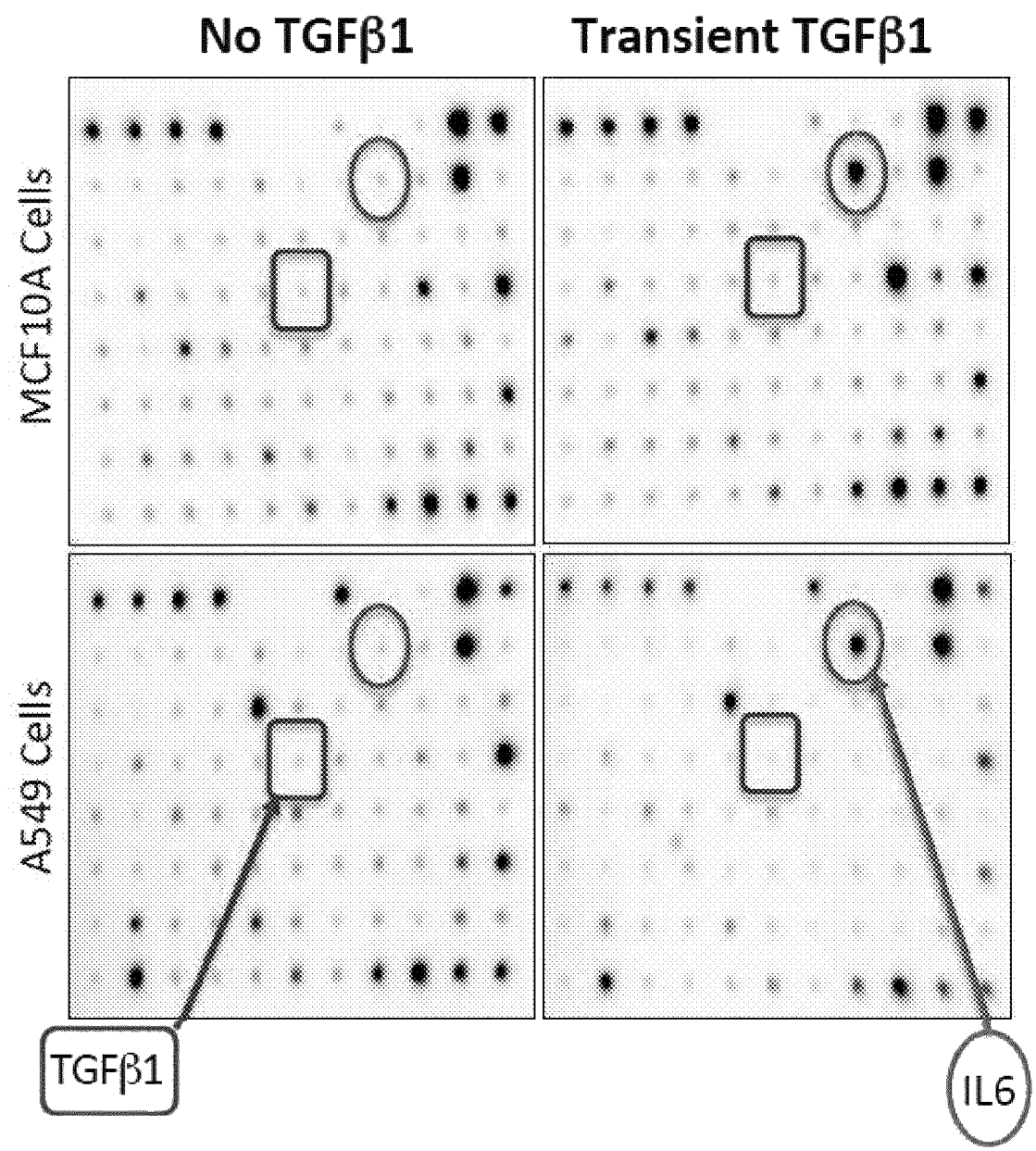
FIGS. 14A and 14B. Twist1 upregulates IL-6 in late EMT. (A) Conditioned media were collected 4d after transient TGFb1 treatment and cytokines determined using a 80-cytokine antibody array (RayBiotech). IL-6 was consistently upregulated in late EMT cells. (B) Cells were infected with a lentivirus expressing control or Twist1 shRNA, and treated with transient TGFb1. RT-PCRs were performed for indicated mRNAs. Twist1 depletion leads to the absence of IL-6 induction.

Studies of EMT in tumor-initiating cells, such as in the lpDTCs, have suggested the presence of autocrine and paracrine cytokine networks critical for prolonged growth suppression of these cells (Ikushima et al., 2009; Jechlinger et al., 2006; Scheel et al., 2011). To test whether a similar autocrine or paracrine cytokine signal is responsible for the high p38 activity in EMT-induced lpDTCs conditioned media from both MCF10A and A549 cells in late EMT were collected and used to induce EMT in parental cells. Conditioned media obtained from Twist1-positive late EMT cells, but not from cells depleted of Twist1, induced EMT, suggesting that Twist1 induces changes in secreted cytokines that maintain EMT (FIG. 13). To identify these cytokines, conditioned media from resting and late EMT cells treated with transient TGFβ1 (MCF10A and A549 cells) were collected and screened for cytokines known to influence p38 or EMT (e.g., PDGF, TGFβ1, EGF, FGF, and IL-6) using an 80-cytokine antibody array (RayBiotech). IL-6 was the only secreted cytokine in this array that was consistently increased in both cell lines during late EMT as compared to resting cells. TGFβ1, a well-known activator of IL-6 (Yao et al., 2010), may be responsible for inducing IL-6 in late EMT as it was used earlier to induce EMT. However, TGFβ1 was not detected in late EMT cells (FIG. 14A); thus IL-6 secretion in late EMT is independent of TGFβ1.

IL-6 is a pro-inflammatory cytokine normally secreted by T cells and macrophages. IL-6 signals through the IL6 (or gp130) family of receptors, which regulates B cell differentiation and the acute phase reaction. IL-6 binding induces receptor dimerization, activating the associated JAKs, which phosphorylate themselves and the receptor. The phosphorylated sites on the receptor and JAKs serve as docking sites for the SH2-containing Stats, such as Stat3, and for SH2-containing proteins and adaptors that link the receptor to MAP kinases (including p38 and ERK1/2), PI3K/Akt, and other pathways. IL-6 has been shown to play regulatory roles in multiple cancers including prostate cancer, multiple myeloma and metastatic cancer (Kishimoto, 2005). Importantly, IL-6 was suggested to be a critical component of an autocrine/paracrine cytokine network regulating stem-like breast cancer cells (Liu et al., 2011). Thus IL-6 is a potential candidate that mediates Twist1-dependent p38 activation and EMT maintenance.

Figure 14B:
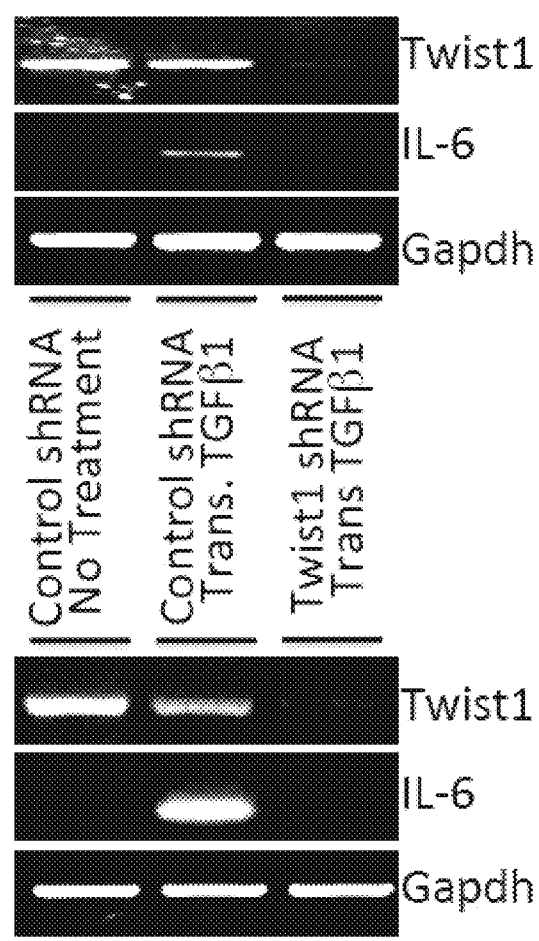
Figure 15:
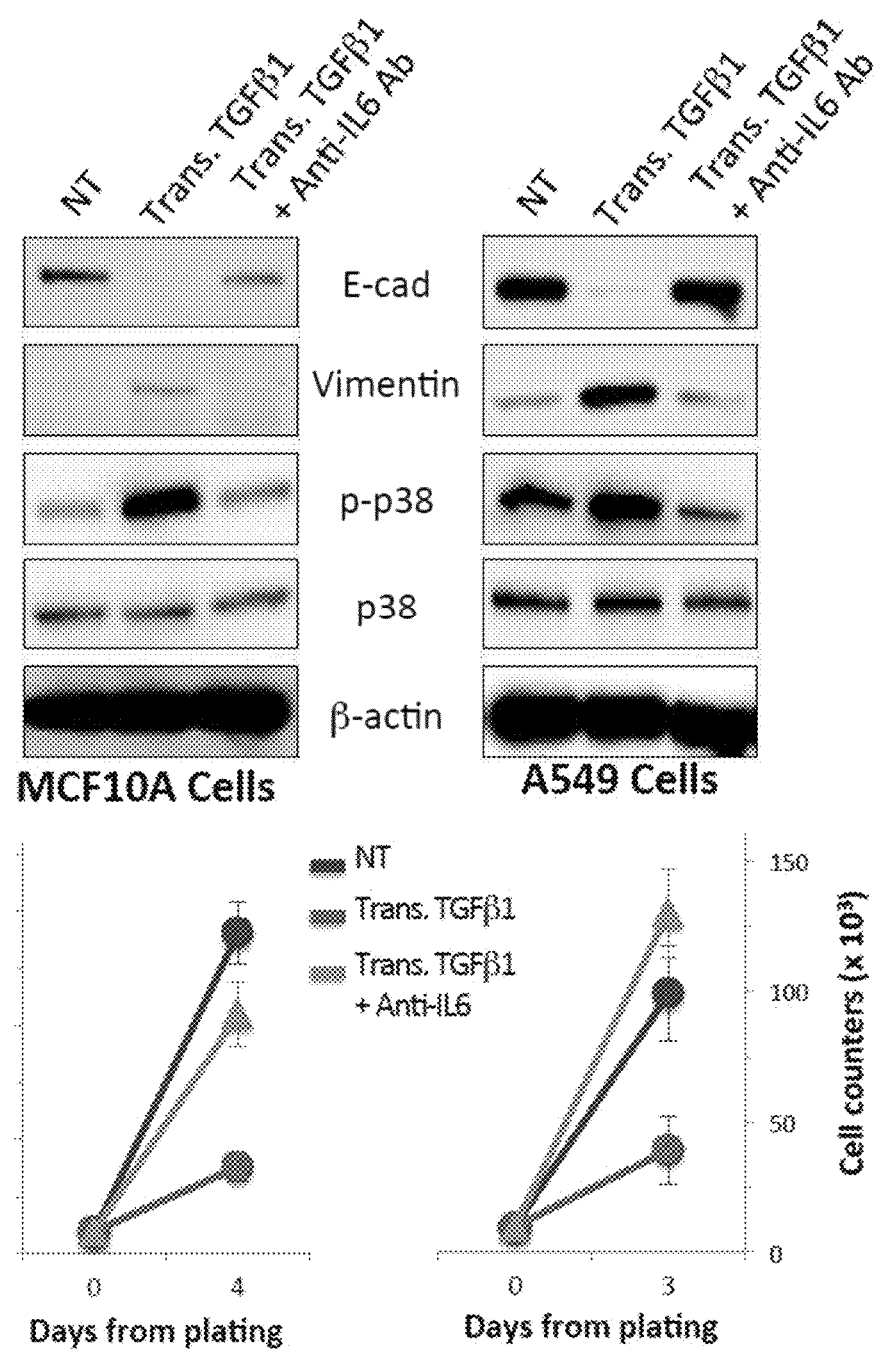
FIG. 15. IL6 is required for late EMT-associated p38 activation and growth arrest. Cells were treated with transient TGFβ1 with or without neutralizing anti-IL6 antibody, and EMT status, p38 phosphorylation and growth determined in late EMT. Anti-IL6 antibody alone or control IgG1 have no effect (not shown).
Figure 16:
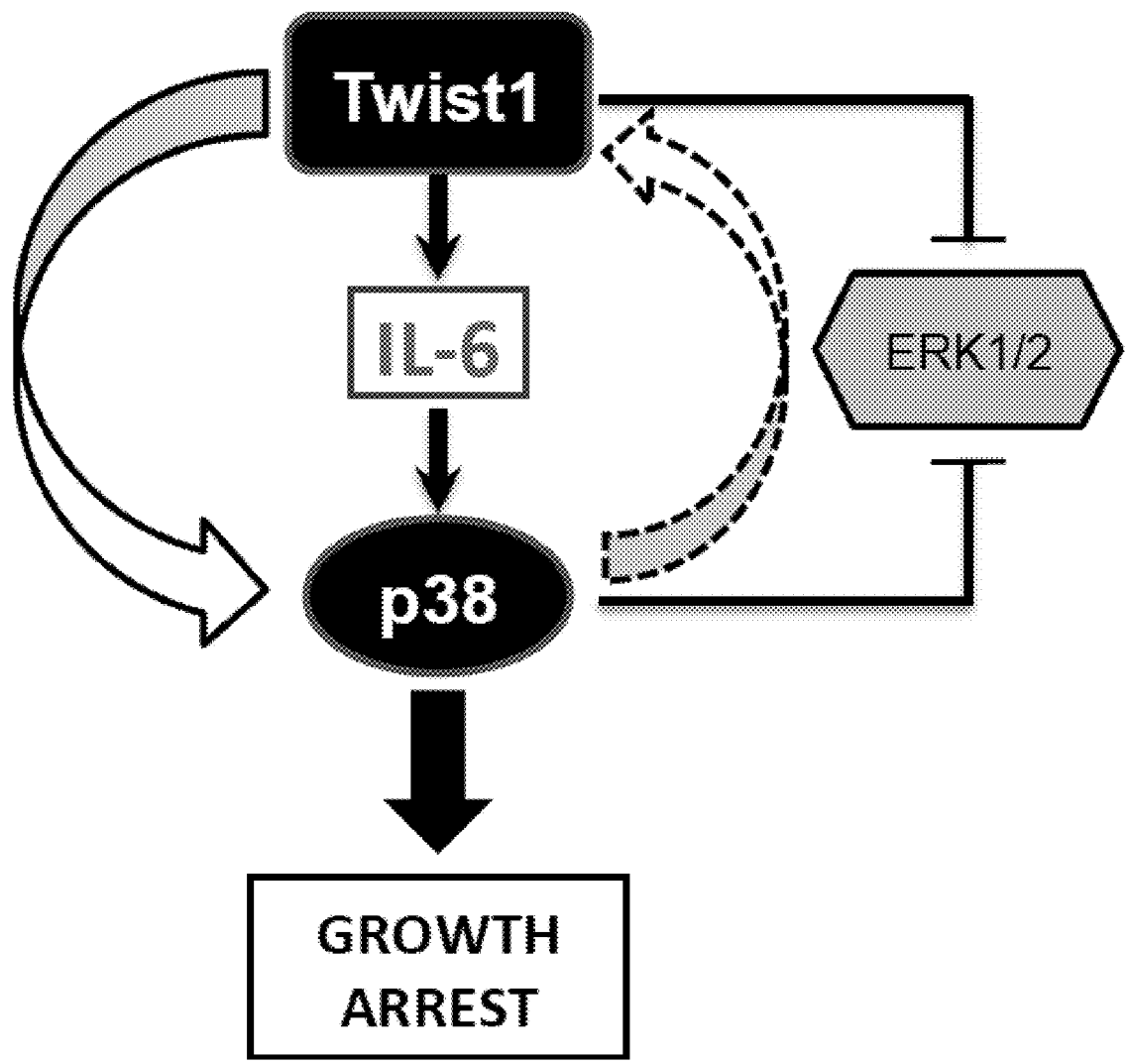
FIG. 16. The Twist1/p38/IL-6 Axis in Maintaining Growth Arrest in Dormant EMT Cells.

To determine whether Twist1 activates IL-6, IL-6 transcript in late EMT cells with or without Twist1 depletion was measured. IL-6 upregulation in late EMT was at the transcriptional level and that Twist1 was required for IL-6 production (FIG. 14B). To determine whether IL-6 has relevant function in EMT maintenance and p38 activation, an IL-6 neutralizing antibody was utilized to inactivate IL-6. Anti-IL-6 antibody was sufficient to reverse late EMT-associated p38 activation and growth arrest (FIG. 15), while anti-IL-6 antibody alone or control IgG1 had no effect. These two key properties of EMT maintenance are also dependent on Twist1 (Tran, 2011). Thus IL-6 appears to be a critical intermediary between Twist1 and p38 (FIG. 16) and thus a natural target to use to break the growth arrest cycle of low proliferative DTCs (lpDTCs) to reawaken them.

Figure 17A:
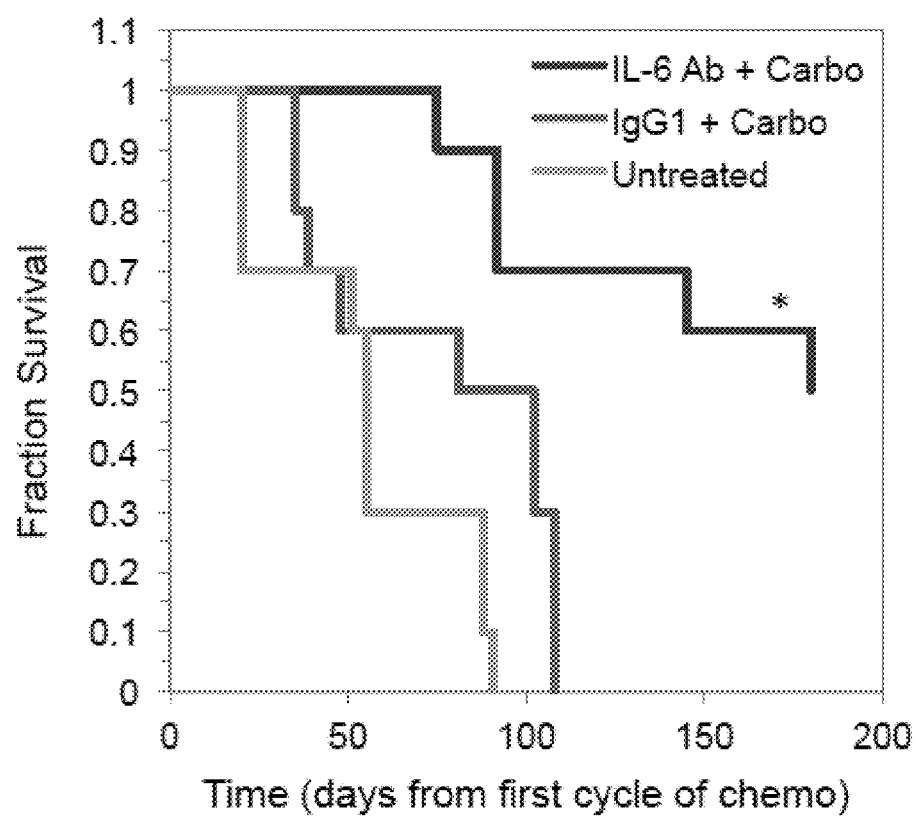
FIGS. 17A and 17B. IL-6 inhibition significantly increases DTCs' sensitivity to carboplatin chemotherapy. BM DTCs-bearing PyMT mice were untreated or treated with Control rat IgG1 followed by carboplatin or with IL-6 neutralizing monoclonal antibody (MP5-20F3) followed by carboplatin. Carboplatin (120 mg/kg) was given IP every 3 weeks for 3 cycles. Anti-IL-6 antibody or control rat IgG1 (250 µg) was given IP once starting 72 hr prior to each carboplatin dosing and repeated once with each carboplatin dosing. Kaplan-Meier estimate of overall survival (Log rank test, *, p<0.05) (A) and total BM DTCs (2 sided T-test, **, p<0.05) (B) before and after treatment were determined.
Figure 17B:
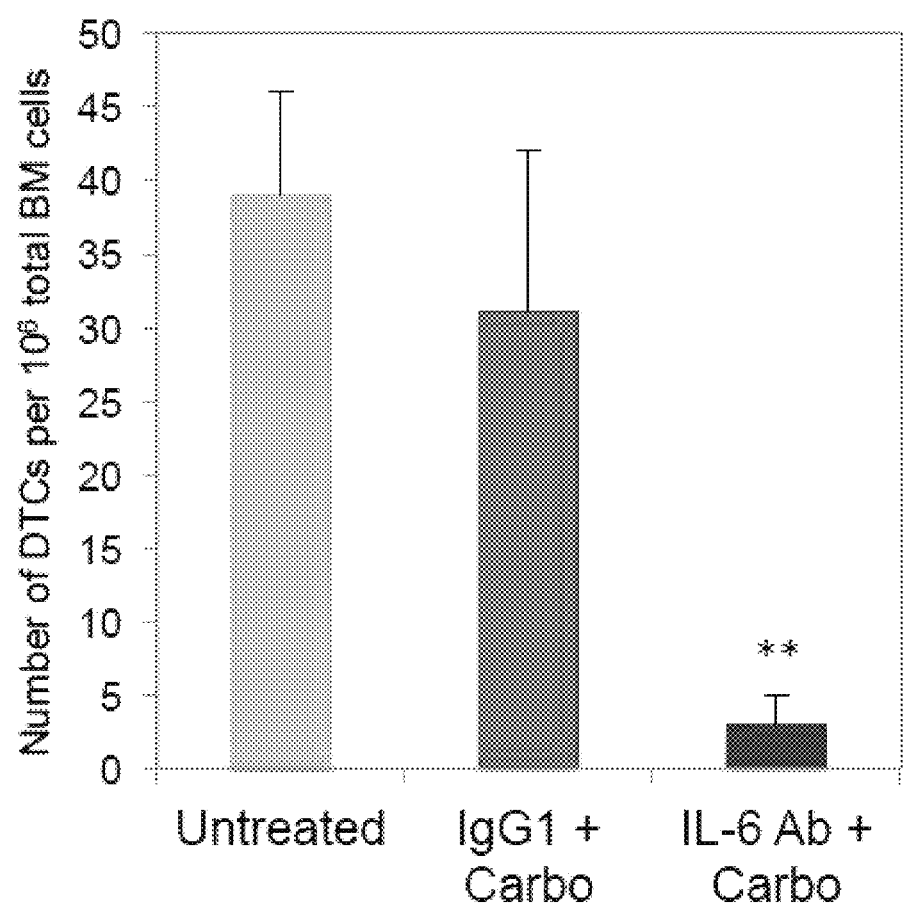

To prove that inhibiting IL-6 was sufficient to make lpDTCs more sensitive to cytotoxic chemotherapy again, PyMT-induced breast cancer mice were treated with either IL-6 neutralizing monoclonal antibody plus carboplatin or carboplatin plus a control IgG1 antibody and the number of BM DTCs and overall survival were measured. For each cycle of treatment, the anti-IL-6 antibody (MP5-20F3) (250 μg) and control rat IgG1 were given intraperitoneally 72 hours prior to and at the same time as carboplatin (120 mg/kg) (FIG. 17A). Three 21-day cycles of treatment were given. Total BM DTCs were determined prior to and 1 week after treatment ended. Pretreatment with the IL-6 neutralizing antibody reduced total BM DTCs and increased overall survival as compared to the rat IgG1 and untreated controls (FIG. 17B).

These results indicate that IL-6 represent a critical signaling intermediary between Twist1 and p38MAPK in the Twist1-dependent EMT maintenance of lpDTCs in breast cancer. Neutralization IL-6 profoundly reversed the growth arrest phenotype of lpDTCs, effectively re-sensitizing them to killing by cytotoxic drugs and making it possible to eliminate these lpDTCs—the main source of early relapses in high-risk breast cancer.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility. It is therefore intended by the appended claims to cover any and all such applications, modifications and embodiments within the scope of the present invention.

Various terms have been defined above. To the extent a term used in a claim is not defined above, it should be given the broadest definition persons in the pertinent art have given that term as reflected in at least one printed publication or issued patent.

All patents, patent applications, published applications and publications, websites and other published materials referred to throughout the entire disclosure herein, unless noted otherwise, are incorporated by reference in their entirety for any purpose.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

As used herein, the use of the singular includes the plural unless specifically stated otherwise. The use of "or" means "and/or" unless stated otherwise. As used herein, use of the term "including" as well as other forms, such as "includes," and "included," is not limiting.

As used herein, "optional" or "optionally" means that the subsequently described event or circumstance does or does not occur, and that the description includes instances where said event or circumstance occurs and instances where it does not. For example, an optional component in a system means that the component may be present or may not be present in the system.

REFERENCES

1. Ikushima, H., Todo, T., Ino, Y., Takahashi, M., Miyazawa, K., and Miyazono, K. (2009). Autocrine TGF-beta Signaling Maintains Tumorigenicity of Glioma-Initiating Cells through Sry-Related HMG-Box Factors. Cell stem cell 5, 504-514.
2. Jechlinger, M., Sommer, A., Moriggl, R., Seither, P., Kraut, N., Capodiecci, P., Donovan, M., Cordon-Cardo, C., Beug, H., and Grunert, S. (2006). Autocrine PDGFR signaling promotes mammary cancer metastasis. J Clin Invest 116, 1561-1570.
3. Kishimoto, T. (2005). Interleukin-6: from basic science to medicine—40 years in immunology. Annual review of immunology 23, 1-21.
4. Liu, S., Ginestier, C., Ou, S. J., Clouthier, S. G., Patel, S. H., Monville, F., Korkaya, H., Heath, A., Dutcher, J., Kleer, C. G., et al. (2011). Breast Cancer Stem Cells Are Regulated by Mesenchymal Stem Cells through Cytokine Networks. Cancer Res 71, 614-624.
5. Scheel, C., Eaton, E. N., Li, S. H.-J., Chaffer, C. L., Reinhardt, F., Kah, K.-J., Bell, G., Guo, W., Rubin, J., Richardson, A. L., et al. (2011). Paracrine and Autocrine Signals Induce and Maintain Mesenchymal and Stem Cell States in the Breast. Cell 145, 926-940.
6. Tran, D. T. C., C. A. S.; Biswas, H; Aft, R. L.; Longmore, G. D. (2011). Temporal and Spatial cooperation of Snail1 and Twist1 during Epithelial-Mesenchymal Transition predicts for human breast cancer recurrence. Molecular Cancer Research In Press.
7. Yao, Z., Fenoglio, S., Gao, D. C., Camiolo, M., Stiles, B., Lindsted, T., Schlederer, M., Johns, C., Altorki, N., Mittal, V., et al. (2010). TGF-OE≤IL-6 axis mediates selective and adaptive mechanisms of resistance to molecular targeted therapy in lung cancer. Proceedings of the National Academy of Sciences.
8. Gupta et al. (2014), *J Biol Chem.*; 289(12): 8706-8719.

What is claimed is:

1. A method of treating a subject having TWIST1 positive low-proliferative disseminated tumor cells (lpDTCs), comprising:
    administering to the subject a therapeutic effective amount of one or more anti-IL-6 receptor (IL-6R) antibodies, and
    administering to the subject a therapeutic effective amount of one or more anticancer cytotoxic drugs or salts thereof,
    wherein the one or more anti-IL-6 receptor antibodies are administered about 1 hour to about 1 week prior to administration of the one or more cytotoxic drugs or salts thereof, and
    wherein administration of the one or more anti-IL-6 receptor (IL-6R) antibodies prior to administration of the one or more cytotoxic drugs or salts thereof increases sensitivity of the lpDTCs to the one or more cytotoxic drugs or salts thereof.

2. The method of claim 1, wherein the one or more cytotoxic drugs are selected from the group consisting of: bendamustine, busulfan, carmustine, chlorambucil, cyclophosphamide, dacarbazine, ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D, dactinomycin, bleomycin, daunorubicin, doxorubicin, doxorubicin (pegylated liposomal), epirubicin, idarubicin, mitomycin, mitoxantrone, etoposide, docetaxel, irinotecan, paclitaxel, topotecan, vinblastine, vincristine, vinorelbine, carboplatin, cisplatin, oxaliplatin, alemtuzamab, bacullus calmette-guerin, bevacizumab, cetuximab, denosumab, erlotinib, gefitinib, imatinib, interferon, ipilimumab, lapatinib, panitumumab, rituximab, sunitinib, sorafenib, temsirolimus, Trastuzumab, clodronate, ibandronic acid, pamidronate, zolendronic acid, anastrozole, abiraterone, amifostine, bexarotene, bicalutamide, buserelin, cyproterone, degarelix, exemestane, flutamide, and folinic acid.

3. The method of claim 1, wherein the lpDTCs are derived from a cancer selected from the group consisting of: breast cancer, pancreas cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma, metastatic skin carcinoma, osteosarcoma, chondrosarcoma, Ewing's sarcoma, malignant fibrous histiocytoma, fibrosarcoma, multiple myeloma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, glioblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, and epidermoid carcinomas.

4. The method of claim 1, wherein the one or more IL-6 pathway inhibitor compounds or salts thereof is administered about 3 days prior to administering the one or more cytotoxic drugs.

5. The method of claim 1, wherein the anti-IL-6R antibody comprises a polyclonal antibody, a monoclonal antibody, a chimeric antibody, or a humanized antibody.

6. The method of claim 5, wherein the anti-IL-6R antibody is selected from the group consisting of: tocilizumab, sarilumab, and ALX-0061.

7. The method of claim 1, wherein the lpDTCs are located in lung or bone marrow.

8. The method of claim 1, wherein the lpDTCs are chemoresistant.

* * * * *